(12) United States Patent
Simonsen et al.

(10) Patent No.: US 12,741,783 B2
(45) Date of Patent: Sep. 22, 2026

(54) LABELING AND PACKAGING SYSTEM AND METHODS

(71) Applicant: C. R. Bard, Inc., Franklin Lakes, NJ (US)

(72) Inventors: Frederick Halden Simonsen, Marietta, GA (US); Tom Roberts, Bishop, GA (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 0 days.

(21) Appl. No.: 18/604,394

(22) Filed: Mar. 13, 2024

(65) Prior Publication Data

US 2025/0289618 A1 Sep. 18, 2025

(51) Int. Cl.
*A61M 25/00* (2006.01)
*A61B 50/30* (2016.01)
(Continued)

(52) U.S. Cl.
CPC ........... *B65D 17/34* (2018.01); *B65D 17/501* (2013.01); *A61B 50/30* (2016.02);
(Continued)

(58) Field of Classification Search
CPC ............ A61M 25/002; A61M 25/0017; A61M 25/0111; A61M 2025/0062; B65D 17/501;
(Continued)

(56) References Cited

U.S. PATENT DOCUMENTS 426,931 A 4/1890 Flower
734,498 A 7/1903 Bachler
(Continued)

FOREIGN PATENT DOCUMENTS

AU 2016283336 A1 12/2017
AU 2014362360 B2 1/2020
(Continued)

OTHER PUBLICATIONS

"Medifilm." Datasheet [online]. Mylan Technologies Inc., 2003 [retrieved on Febuary 14, 2020]. Retrieved from the Internet: <URL: https://web.archive.org/web/20030205090818/http://www.mylantech.com/products/medifilm.html>.
(Continued)

*Primary Examiner* — Gideon R Weinerth
(74) *Attorney, Agent, or Firm* — Rutan & Tucker LLP

(57) ABSTRACT

Labeling and packaging systems include a primary packaging with a top seam and a bottom seam, and enclosing a medical device within its interior cavity. The system further comprises a label system, which consists of a first body with a front surface and a rear surface, extending over a frontal plane and attached to the front surface of the primary packaging. Additionally, the label system includes a first right handle and a first left handle, both attached to the top edge of the first body. A tear line extends longitudinally from the top edge of the first body, and is disposed between the right handle and the left handle. The tear line has a distance (d) that is less than a length (L) of the first body. The tear line is designed to facilitate separation when the right handle is pulled in the opposite direction from the left handle.

20 Claims, 7 Drawing Sheets

(51) Int. Cl.

| | |
|---|---|
| ***B65D 17/34*** | (2006.01) |
| ***B65D 17/50*** | (2006.01) |
| ***B65D 33/08*** | (2006.01) |
| ***B65D 75/00*** | (2006.01) |
| ***B65D 75/58*** | (2006.01) |

(52) U.S. Cl.

CPC .... *A61B 2050/314* (2016.02); *A61M 25/0017* (2013.01); *A61M 25/002* (2013.01); *B65D 2203/02* (2013.01)

(58) Field of Classification Search

CPC .... B65D 17/4012; B65D 27/34; B65D 27/36; B65D 33/08; B65D 75/30; B65D 2203/02; B65D 2575/3227; B65D 17/34; B65D 25/28; B65D 75/58; B65D 75/5833; B65D 75/5855; A61B 50/30; A61B 2050/0065; A61B 2050/314

USPC ........ 206/364, 210; 229/200, 307, 309, 310, 229/87.05; 604/544

See application file for complete search history.

(56) References Cited

U.S. PATENT DOCUMENTS 1,131,865 A 3/1915 Putnam et al.
1,235,142 A 7/1917 Ichilian
1,304,396 A 5/1919 Smith
1,643,289 A 9/1927 Peglay
1,661,494 A 3/1928 Nielsen
1,876,229 A 9/1932 Oliver et al.
1,888,349 A 11/1932 Jacoby
1,978,497 A 10/1934 Lind
2,043,630 A 6/1936 Raiche
2,213,210 A 9/1940 Egbert
2,228,992 A 1/1941 Fry
2,230,226 A 2/1941 Auzin
2,248,934 A 7/1941 Auzin
2,262,749 A 11/1941 Berwald
2,285,502 A 6/1942 Dreyfus
2,308,484 A 1/1943 Auzin et al.
2,314,262 A 3/1943 Winder
2,320,157 A 5/1943 Raiche
2,322,858 A 6/1943 Limbert et al.
2,330,399 A 9/1943 Winder
2,330,400 A 9/1943 Winder
2,389,831 A 11/1945 Welsh
2,390,070 A 12/1945 Auzin
2,481,488 A 9/1949 Auzin
2,494,393 A 1/1950 Lamson
2,610,626 A 9/1952 Edwards
2,638,093 A 5/1953 Kulick
2,648,463 A * 8/1953 Scherer ............. B65D 75/5855 222/541.9
2,649,619 A 8/1953 Killian
2,649,854 A 8/1953 Salm
2,690,595 A 10/1954 Raiche
2,712,161 A 7/1955 Moss
2,856,932 A 10/1958 Griffitts
2,912,981 A 11/1959 Keough
2,919,697 A 1/1960 Kim
3,035,691 A * 5/1962 Rasmussen ......... A61M 25/002 206/484
3,044,468 A 7/1962 Birtwell
3,053,257 A 9/1962 Birtwell
3,076,464 A 2/1963 Rosenberg
3,169,527 A 2/1965 Sheridan
3,173,566 A 3/1965 Talbert
3,211,151 A 10/1965 Foderick et al.
3,246,075 A 4/1966 Dansard
3,249,285 A * 5/1966 Dollheimer ........... B65D 33/08 383/9
3,304,353 A 2/1967 Harautuneian
3,344,791 A 10/1967 Foderick
3,345,988 A 10/1967 Vitello
3,394,704 A 7/1968 Dery
3,394,705 A 7/1968 Abramson
3,403,682 A 10/1968 McDonell
3,409,016 A 11/1968 Foley
3,434,869 A 3/1969 Davidson
3,463,141 A 8/1969 Mozolf
3,478,743 A 11/1969 Ericson
3,503,400 A 3/1970 Osthagen
3,508,959 A 4/1970 Krahnke
3,509,884 A 5/1970 Bell
3,520,305 A 7/1970 Davis
3,539,674 A 11/1970 Dereniuk et al.
3,544,668 A 12/1970 Dereniuk
3,548,805 A 12/1970 Datsenko
3,556,294 A 1/1971 Walck et al.
3,556,874 A 1/1971 McClain
3,566,874 A 3/1971 Shepherd et al.
3,593,713 A 7/1971 Bogoff et al.
3,598,127 A 8/1971 Wepsic
3,606,889 A 9/1971 Arblaster
3,642,004 A 2/1972 Osthagen et al.
3,646,929 A 3/1972 Bonnar
3,648,704 A 3/1972 Jackson
3,648,891 A 3/1972 Katz et al.
3,651,615 A * 3/1972 Bohner .............. B29C 65/7891 493/203
3,683,928 A 8/1972 Kuntz
3,695,921 A 10/1972 Shepherd et al.
3,699,956 A 10/1972 Kitrilakis et al.
3,699,964 A 10/1972 Ericson
3,708,324 A 1/1973 Stebleton
3,726,281 A 4/1973 Norton et al.
3,739,783 A 6/1973 Broerman
3,761,013 A 9/1973 Schuster
3,762,399 A 10/1973 Riedell
3,768,102 A 10/1973 Kwan-Gett et al.
3,788,324 A 1/1974 Lim
3,794,042 A 2/1974 De Klotz et al.
3,797,478 A 3/1974 Walsh et al.
3,802,987 A 4/1974 Noll
3,835,992 A 9/1974 Adams, IV
3,838,728 A 10/1974 Voegele
3,841,304 A 10/1974 Jones
3,854,483 A 12/1974 Powers
3,861,395 A 1/1975 Taniguchi
3,875,937 A 4/1975 Schmitt et al.
3,879,516 A 4/1975 Wolvek
3,882,220 A 5/1975 Ryder
3,889,685 A 6/1975 Miller, Jr. et al.
3,894,540 A 7/1975 Bonner, Jr.
3,898,993 A 8/1975 Taniguchi
3,924,634 A 12/1975 Taylor et al.
3,926,309 A 12/1975 Center
3,926,705 A 12/1975 Todd
3,930,580 A 1/1976 Bazell et al.
3,934,721 A 1/1976 Juster et al.
3,962,519 A 6/1976 Rusch et al.
3,967,728 A 7/1976 Gordon et al.
3,981,299 A 9/1976 Murray
3,983,879 A 10/1976 Todd
4,026,296 A 5/1977 Stoy et al.
4,029,104 A 6/1977 Kerber
4,051,849 A 10/1977 Poncy et al.
4,055,682 A 10/1977 Merrill
4,062,363 A 12/1977 Bonner, Jr.
4,069,359 A 1/1978 DeMarse et al.
4,091,922 A 5/1978 Egler
4,119,094 A 10/1978 Micklus et al.
4,120,715 A 10/1978 Ockwell et al.
4,133,303 A 1/1979 Patel
4,140,127 A 2/1979 Cianci et al.
4,149,539 A 4/1979 Cianci
4,168,699 A 9/1979 Hauser
4,170,996 A 10/1979 Wu
4,186,745 A 2/1980 Lewis et al.
4,187,851 A 2/1980 Hauser
4,196,731 A 4/1980 Laurin et al.
4,198,983 A 4/1980 Becker et al.

(56) References Cited

U.S. PATENT DOCUMENTS 4,198,984 A 4/1980 Taylor
4,209,010 A 6/1980 Ward et al.
4,225,371 A 9/1980 Taylor et al.
4,230,115 A 10/1980 Walz, Jr. et al.
4,245,639 A 1/1981 La Rosa
4,246,909 A 1/1981 Wu et al.
4,249,535 A 2/1981 Hargest, III
4,252,760 A 2/1981 Foster et al.
4,265,848 A 5/1981 Rusch
4,266,999 A 5/1981 Baier
4,269,310 A 5/1981 Uson
4,284,459 A 8/1981 Patel et al.
4,287,227 A 9/1981 Kamada et al.
4,306,557 A 12/1981 North
4,311,146 A 1/1982 Wonder
4,311,659 A 1/1982 Rey et al.
4,318,406 A 3/1982 McLeod
4,318,947 A 3/1982 Joung
4,341,817 A 7/1982 Tozier et al.
4,343,788 A 8/1982 Mustacich et al.
4,350,161 A 9/1982 Davis, Jr.
4,351,333 A 9/1982 Lazarus et al.
4,366,901 A 1/1983 Short
4,367,732 A 1/1983 Poulsen et al.
4,378,018 A 3/1983 Alexander et al.
4,378,796 A 4/1983 Milhaud
4,379,506 A 4/1983 Davidson
4,381,008 A 4/1983 Thomas et al.
4,381,380 A 4/1983 LeVeen et al.
4,392,848 A 7/1983 Lucas et al.
4,395,806 A 8/1983 Wonder et al.
4,411,648 A 10/1983 Davis et al.
4,419,097 A 12/1983 Rowland
4,428,365 A 1/1984 Hakky
4,449,971 A 5/1984 Cawood
4,457,299 A 7/1984 Cornwell
4,472,226 A 9/1984 Redinger et al.
4,475,910 A 10/1984 Conway et al.
4,477,325 A 10/1984 Osburn
4,479,795 A 10/1984 Mustacich et al.
4,486,504 A 12/1984 Chung
4,496,354 A 1/1985 Steer et al.
4,515,593 A 5/1985 Norton
4,517,971 A 5/1985 Sorbonne
4,534,768 A 8/1985 Osburn et al.
4,539,234 A 9/1985 Sakamoto et al.
4,540,409 A 9/1985 Nystrom et al.
4,552,269 A 11/1985 Chang
4,553,533 A 11/1985 Leighton
4,560,382 A 12/1985 Isono et al.
4,563,184 A 1/1986 Korol
4,568,340 A 2/1986 Giacalone
4,571,239 A 2/1986 Heyman
4,571,240 A 2/1986 Samson et al.
4,571,241 A 2/1986 Christopher
4,576,599 A 3/1986 Lipner
4,581,026 A 4/1986 Schneider
4,581,028 A 4/1986 Fox, Jr. et al.
4,582,762 A 4/1986 Onohara et al.
4,585,666 A 4/1986 Lambert
4,586,974 A 5/1986 Nystrom et al.
4,589,874 A 5/1986 Riedel et al.
4,592,920 A 6/1986 Murtfeldt
4,597,765 A 7/1986 Klatt
4,597,931 A 7/1986 Watanabe et al.
4,601,713 A 7/1986 Fuqua
4,603,152 A 7/1986 Laurin et al.
4,607,746 A 8/1986 Stinnette
4,610,670 A 9/1986 Spencer
4,612,337 A 9/1986 Fox, Jr. et al.
4,613,324 A 9/1986 Ghajar
4,615,692 A 10/1986 Giacalone et al.
4,615,697 A 10/1986 Robinson
4,619,642 A 10/1986 Spencer
4,622,033 A 11/1986 Taniguchi
4,623,329 A 11/1986 Drobish et al.
4,626,250 A 12/1986 Schneider
4,627,844 A 12/1986 Schmitt
4,634,433 A 1/1987 Osborne
4,637,907 A 1/1987 Hegel et al.
4,638,790 A 1/1987 Conway et al.
4,639,246 A 1/1987 Dudley
4,640,688 A 2/1987 Hauser
4,652,259 A 3/1987 O'Neil
4,664,657 A 5/1987 Williamitis et al.
4,673,401 A 6/1987 Jensen et al.
4,677,143 A 6/1987 Laurin et al.
4,681,572 A 7/1987 Tokarz et al.
4,685,913 A 8/1987 Austin
4,686,124 A 8/1987 Onohara et al.
4,687,470 A 8/1987 Okada
4,692,152 A 9/1987 Emde
4,692,154 A 9/1987 Singery et al.
4,696,672 A 9/1987 Mochizuki et al.
4,699,616 A 10/1987 Nowak et al.
4,704,102 A 11/1987 Guthery
4,710,169 A 12/1987 Christopher
4,710,181 A 12/1987 Fuqua
4,723,946 A 2/1988 Kay
4,731,064 A 3/1988 Heyden
4,737,219 A 4/1988 Taller et al.
4,738,667 A 4/1988 Galloway
4,739,768 A 4/1988 Engelson
4,747,845 A 5/1988 Korol
4,754,877 A 7/1988 Johansson et al.
4,759,753 A 7/1988 Schneider et al.
4,762,128 A 8/1988 Rosenbluth
4,769,013 A 9/1988 Lorenz et al.
4,769,099 A 9/1988 Therriault et al.
4,772,473 A 9/1988 Patel et al.
4,773,901 A 9/1988 Norton
4,775,371 A 10/1988 Mueller, Jr.
4,784,651 A 11/1988 Hickey et al.
4,790,834 A 12/1988 Austin
4,790,835 A 12/1988 Elias
D299,865 S 2/1989 Kamstrup-Larsen et al.
4,810,247 A 3/1989 Glassman
4,811,847 A 3/1989 Reif et al.
4,813,935 A 3/1989 Haber et al.
4,820,270 A 4/1989 Hardcastle et al.
4,820,289 A 4/1989 Coury et al.
4,820,291 A 4/1989 Terauchi et al.
4,820,292 A 4/1989 Korol et al.
4,834,721 A 5/1989 Onohara et al.
4,838,876 A 6/1989 Wong et al.
4,846,784 A 7/1989 Haber
4,846,909 A 7/1989 Klug et al.
4,850,969 A 7/1989 Jackson
4,861,337 A 8/1989 George
4,863,424 A 9/1989 Blake, III et al.
4,863,444 A 9/1989 Blomer
4,863,449 A 9/1989 Therriault et al.
4,867,748 A 9/1989 Samuelsen
4,874,373 A 10/1989 Luther et al.
4,876,109 A 10/1989 Mayer et al.
4,885,049 A 12/1989 Johannesson
4,886,508 A 12/1989 Washington
4,888,005 A 12/1989 Dingeman et al.
4,893,623 A 1/1990 Rosenbluth
4,894,059 A 1/1990 Larsen et al.
4,902,503 A 2/1990 Umemura et al.
4,904,260 A 2/1990 Ray et al.
4,917,113 A 4/1990 Conway et al.
4,917,686 A 4/1990 Bayston et al.
RE33,206 E 5/1990 Conway et al.
4,923,450 A 5/1990 Maeda et al.
4,925,668 A 5/1990 Khan et al.
4,930,522 A 6/1990 Busnel et al.
4,931,056 A 6/1990 Ghajar et al.
4,932,938 A 6/1990 Goldberg et al.
4,932,948 A 6/1990 Kernes et al.
4,934,999 A 6/1990 Bader
4,935,260 A 6/1990 Shlenker
4,950,256 A 8/1990 Luther et al.

(56) References Cited

U.S. PATENT DOCUMENTS 4,957,487 A 9/1990 Gerow
4,963,137 A 10/1990 Heyden
4,968,294 A 11/1990 Salama
4,968,507 A 11/1990 Zentner et al.
4,976,703 A 12/1990 Franetzki et al.
4,981,471 A 1/1991 Quinn et al.
4,994,047 A 2/1991 Walker et al.
4,997,426 A 3/1991 Dingeman et al.
5,001,009 A 3/1991 Whitbourne
5,004,454 A 4/1991 Beyar et al.
5,007,897 A 4/1991 Kalb et al.
5,013,306 A 5/1991 Solomon et al.
5,013,717 A 5/1991 Solomon et al.
5,019,096 A 5/1991 Fox, Jr. et al.
5,019,378 A 5/1991 Allen
5,019,601 A 5/1991 Allen
5,045,078 A 9/1991 Asta
5,059,190 A 10/1991 Novak
5,062,716 A * 11/1991 Conrad .................. B65D 33/14 383/22
5,071,406 A 12/1991 Jang
5,077,352 A 12/1991 Elton
5,078,707 A 1/1992 Peter Klug
5,082,006 A 1/1992 Jonasson
5,084,037 A 1/1992 Barnett
5,087,252 A 2/1992 Denard
5,088,980 A 2/1992 Leighton
5,089,205 A 2/1992 Huang et al.
5,090,424 A 2/1992 Simon et al.
5,098,379 A 3/1992 Conway et al.
5,100,396 A 3/1992 Zamierowski
5,102,401 A 4/1992 Lambert et al.
5,102,405 A 4/1992 Conway et al.
5,109,378 A 4/1992 Proctor et al.
5,109,601 A 5/1992 McBride
5,112,306 A 5/1992 Burton et al.
5,114,398 A 5/1992 Trick et al.
5,118,007 A 6/1992 Lewis et al.
5,128,088 A 7/1992 Shimomura et al.
5,131,906 A 7/1992 Chen
5,137,671 A 8/1992 Conway et al.
5,140,999 A 8/1992 Ardito
5,147,341 A 9/1992 Starke et al.
5,165,952 A 11/1992 Solomon et al.
5,174,290 A 12/1992 Fiddian-Green
5,176,666 A 1/1993 Conway et al.
5,179,174 A 1/1993 Elton
5,180,591 A 1/1993 Magruder et al.
5,186,172 A 2/1993 Fiddian-Green
5,188,596 A 2/1993 Condon et al.
5,197,957 A 3/1993 Wendler
5,201,724 A 4/1993 Hukins et al.
5,209,726 A 5/1993 Goosen
5,209,728 A 5/1993 Kraus et al.
5,211,640 A 5/1993 Wendler
5,224,953 A 7/1993 Morgentaler
5,226,530 A 7/1993 Golden
5,234,411 A 8/1993 Vaillancourt et al.
5,236,422 A 8/1993 Eplett, Jr.
5,242,391 A 9/1993 Place et al.
5,242,398 A 9/1993 Knoll et al.
5,242,428 A 9/1993 Palestrant
5,261,896 A 11/1993 Conway et al.
5,263,947 A 11/1993 Kay
5,269,755 A 12/1993 Bodicky
5,269,770 A 12/1993 Conway et al.
5,270,358 A 12/1993 Asmus
5,282,795 A 2/1994 Finney
5,290,306 A 3/1994 Trotta et al.
5,306,226 A 4/1994 Salama
5,334,175 A 8/1994 Conway et al.
5,336,211 A 8/1994 Metz
5,346,483 A 9/1994 Thaxton, Sr.
5,348,536 A 9/1994 Young et al.
5,352,182 A 10/1994 Kalb et al.
5,354,132 A 10/1994 Young et al.
5,360,402 A 11/1994 Conway et al.
5,360,414 A 11/1994 Yarger
5,366,449 A 11/1994 Gilberg
5,368,575 A 11/1994 Chang
5,370,899 A 12/1994 Conway et al.
5,376,085 A 12/1994 Conway et al.
5,380,312 A 1/1995 Goulter
5,395,333 A 3/1995 Brill
5,409,014 A 4/1995 Napoli et al.
5,409,495 A 4/1995 Osborn
5,415,165 A 5/1995 Fiddian-Green
5,415,635 A 5/1995 Bagaoisan et al.
5,417,226 A 5/1995 Juma
5,417,666 A 5/1995 Coulter
5,423,784 A 6/1995 Metz
5,433,705 A 7/1995 Giebel et al.
5,433,713 A 7/1995 Trotta
5,445,626 A 8/1995 Gigante et al.
5,447,231 A 9/1995 Kastenhofer
5,451,424 A 9/1995 Solomon et al.
5,454,798 A 10/1995 Kubalak et al.
5,456,251 A 10/1995 Fiddian-Green
5,464,650 A 11/1995 Berg et al.
5,466,229 A 11/1995 Elson et al.
5,476,434 A 12/1995 Kalb et al.
5,479,945 A 1/1996 Simon
5,482,740 A 1/1996 Conway et al.
5,483,976 A 1/1996 McLaughlin et al.
5,497,601 A 3/1996 Gonzalez
5,501,669 A 3/1996 Conway et al.
5,509,427 A 4/1996 Simon et al.
5,509,889 A 4/1996 Kalb et al.
5,509,899 A 4/1996 Fan et al.
5,513,659 A 5/1996 Buuck et al.
5,513,660 A 5/1996 Simon et al.
5,514,112 A 5/1996 Chu et al.
5,520,636 A 5/1996 Korth et al.
5,531,715 A 7/1996 Engelson et al.
5,531,717 A 7/1996 Roberto et al.
5,536,258 A 7/1996 Folden
5,538,584 A 7/1996 Metz
5,554,140 A 9/1996 Michels et al.
5,554,141 A 9/1996 Wendler
5,558,900 A 9/1996 Fan et al.
5,562,599 A 10/1996 Beyschlag
5,567,495 A 10/1996 Modak et al.
5,569,219 A 10/1996 Hakki et al.
5,582,599 A 12/1996 Daneshvar
5,591,292 A 1/1997 Blomqvist
5,593,718 A 1/1997 Conway et al.
5,599,321 A 2/1997 Conway et al.
5,601,537 A 2/1997 Frassica
5,607,417 A 3/1997 Batich et al.
5,614,143 A 3/1997 Hager
5,616,126 A 4/1997 Malekmehr et al.
5,620,109 A 4/1997 Madden
5,624,395 A 4/1997 Mikhail et al.
5,630,429 A 5/1997 Dann
5,643,235 A 7/1997 Figuerido
5,645,048 A 7/1997 Brodsky et al.
5,653,700 A 8/1997 Byrne et al.
5,670,111 A 9/1997 Conway et al.
5,671,755 A 9/1997 Simon et al.
5,688,516 A 11/1997 Raad et al.
5,695,456 A 12/1997 Cartmell et al.
5,695,485 A 12/1997 Duperret et al.
5,702,381 A 12/1997 Cottenden
5,704,353 A 1/1998 Kalb et al.
5,707,357 A 1/1998 Mikhail et al.
5,709,672 A 1/1998 Illner
5,711,841 A 1/1998 Jaker
5,724,994 A 3/1998 Simon et al.
5,730,733 A 3/1998 Mortier et al.
5,736,152 A 4/1998 Dunn
5,749,826 A 5/1998 Faulkner
5,752,525 A 5/1998 Simon et al.
5,756,144 A 5/1998 Wolff et al.
5,762,996 A 6/1998 Lucas et al.

(56) References Cited

U.S. PATENT DOCUMENTS 5,779,670 A 7/1998 Bidwell et al.
5,782,808 A 7/1998 Folden
5,785,694 A 7/1998 Cohen et al.
5,788,687 A 8/1998 Batich et al.
5,789,018 A 8/1998 Engelson et al.
5,795,332 A 8/1998 Lucas et al.
5,795,334 A 8/1998 Cochrane, III
5,795,524 A 8/1998 Basso, Jr. et al.
5,800,339 A 9/1998 Salama
5,806,527 A 9/1998 Borodulin et al.
5,810,789 A 9/1998 Powers et al.
5,817,067 A 10/1998 Tsukada et al.
5,820,583 A 10/1998 Demopulos et al.
5,820,607 A 10/1998 Tcholakian et al.
5,827,247 A 10/1998 Kay
5,827,249 A 10/1998 Jensen
5,830,932 A 11/1998 Kay
5,840,151 A 11/1998 Munsch
5,848,691 A 12/1998 Morris et al.
5,853,518 A 12/1998 Utas
5,871,475 A 2/1999 Frassica
5,877,243 A 3/1999 Sarangapani
5,895,374 A 4/1999 Rodsten
5,897,535 A 4/1999 Feliziani et al.
5,902,631 A 5/1999 Wang et al.
5,906,575 A 5/1999 Conway et al.
5,919,170 A 7/1999 Woessner
5,941,856 A 8/1999 Kovacs et al.
5,958,167 A 9/1999 Van Driel et al.
5,971,954 A 10/1999 Conway et al.
5,980,483 A 11/1999 Dimitri
5,980,507 A 11/1999 Fassuliotis et al.
5,989,230 A 11/1999 Frassica
5,997,517 A 12/1999 Whitbourne
6,004,305 A 12/1999 Hursman et al.
6,007,521 A 12/1999 Bidwell et al.
6,007,524 A 12/1999 Schneider
6,007,526 A 12/1999 Passalaqua et al.
6,024,751 A 2/2000 Lovato et al.
6,050,934 A 4/2000 Mikhail et al.
6,053,905 A 4/2000 Daignault, Jr. et al.
6,056,715 A 5/2000 Demopulos et al.
6,059,107 A 5/2000 Nosted et al.
6,063,063 A 5/2000 Harboe et al.
6,065,597 A 5/2000 Pettersson et al.
6,070,275 A 6/2000 Garlock
6,090,075 A 7/2000 House
6,097,976 A 8/2000 Yang et al.
6,102,929 A 8/2000 Conway et al.
6,113,582 A 9/2000 Dwork
6,119,697 A 9/2000 Engel et al.
6,131,575 A 10/2000 Lenker et al.
6,132,399 A 10/2000 Shultz
6,156,049 A 12/2000 Lovato et al.
6,162,201 A 12/2000 Cohen et al.
6,183,461 B1 2/2001 Matsuura et al.
6,186,990 B1 2/2001 Chen et al.
6,190,353 B1 2/2001 Makower et al.
6,206,885 B1 3/2001 Ghahremani et al.
6,210,394 B1 4/2001 Demopulos et al.
6,217,569 B1 4/2001 Fiore
6,221,056 B1 4/2001 Silverman
6,231,501 B1 5/2001 Ditter
6,238,383 B1 5/2001 Karram et al.
6,254,570 B1 7/2001 Rutner et al.
6,254,582 B1 7/2001 O'Donnell et al.
6,254,585 B1 7/2001 Demopulos et al.
6,256,525 B1 7/2001 Yang et al.
6,261,255 B1 7/2001 Mullis et al.
6,261,271 B1 7/2001 Solomon et al.
6,261,279 B1 7/2001 Demopulos et al.
6,270,902 B1 8/2001 Tedeschi et al.
6,280,425 B1 8/2001 Del Guercio
6,287,285 B1 9/2001 Michal et al.
6,293,923 B1 9/2001 Yachia et al.
6,296,627 B1 10/2001 Edwards
6,299,598 B1 10/2001 Bander
6,306,176 B1 10/2001 Whitbourne
6,306,422 B1 10/2001 Batich et al.
6,309,104 B1 * 10/2001 Koch .................... B65D 75/58
383/200
6,315,711 B1 11/2001 Conway et al.
6,329,488 B1 12/2001 Terry et al.
6,340,359 B1 1/2002 Silverman
6,340,465 B1 1/2002 Hsu et al.
6,355,004 B1 3/2002 Pedersen et al.
6,358,229 B1 3/2002 Tihon
6,368,315 B1 4/2002 Gillis et al.
6,368,317 B2 4/2002 Chang
6,379,334 B1 4/2002 Frassica
6,383,434 B2 5/2002 Conway et al.
6,387,080 B1 5/2002 Rodsten
6,391,010 B1 5/2002 Wilcox
6,391,014 B1 5/2002 Silverman
6,398,718 B1 6/2002 Yachia et al.
6,402,726 B1 6/2002 Genese
6,409,717 B1 6/2002 Israelsson et al.
6,423,041 B1 7/2002 Grant
6,437,038 B1 8/2002 Chen
6,440,060 B1 8/2002 Latour, Jr.
6,458,867 B1 10/2002 Wang et al.
6,468,245 B2 10/2002 Alexandersen
6,479,000 B2 11/2002 Conway et al.
6,479,726 B1 11/2002 Cole
6,485,476 B1 11/2002 von Dyck et al.
6,509,319 B1 1/2003 Raad et al.
6,544,240 B1 4/2003 Borodulin et al.
6,551,293 B1 4/2003 Mitchell
6,558,369 B2 5/2003 Rosenblum
6,558,792 B1 5/2003 Vaabengaard et al.
6,558,798 B2 5/2003 Zhong et al.
6,578,709 B1 6/2003 Kavanagh et al.
6,579,539 B2 6/2003 Lawson et al.
6,582,401 B1 6/2003 Windheuser et al.
6,596,401 B1 7/2003 Terry et al.
6,602,244 B2 8/2003 Kavanagh et al.
6,613,014 B1 9/2003 Chi
6,613,342 B2 9/2003 Aoki
6,626,888 B1 9/2003 Conway et al.
6,629,969 B2 10/2003 Chan et al.
6,632,204 B2 10/2003 Guldfeldt et al.
6,634,498 B2 10/2003 Kayerod et al.
6,638,269 B2 10/2003 Wilcox
6,648,906 B2 11/2003 Lasheras et al.
6,659,937 B2 12/2003 Polsky et al.
6,682,555 B2 1/2004 Cioanta et al.
6,693,189 B2 2/2004 Holt et al.
6,695,831 B1 2/2004 Tsukada et al.
6,706,025 B2 3/2004 Engelson et al.
6,711,436 B1 3/2004 Duhaylongsod
6,716,895 B1 4/2004 Terry
6,719,709 B2 4/2004 Whalen et al.
6,723,350 B2 4/2004 Burrell et al.
6,730,113 B2 5/2004 Eckhardt et al.
6,733,474 B2 5/2004 Kusleika
6,736,805 B2 5/2004 Israelsson et al.
6,740,273 B2 5/2004 Lee
6,746,421 B2 6/2004 Yachia et al.
6,767,551 B2 7/2004 McGhee et al.
6,780,504 B2 8/2004 Rupprecht et al.
6,783,520 B1 8/2004 Candray et al.
D496,266 S 9/2004 Nestenborg
6,787,156 B1 9/2004 Bar-Shalom
6,797,743 B2 9/2004 McDonald et al.
6,824,532 B2 11/2004 Gillis et al.
6,835,183 B2 12/2004 Lennox et al.
6,835,410 B2 12/2004 Chabrecek et al.
6,840,379 B2 1/2005 Franks-Farah et al.
6,848,574 B1 2/2005 Israelsson et al.
6,849,070 B1 2/2005 Hansen et al.
6,852,098 B2 2/2005 Byrne
6,852,105 B2 2/2005 Bolmsjo et al.
D503,335 S 3/2005 Risberg et al.
6,869,416 B2 3/2005 Windheuser et al.

(56) References Cited

U.S. PATENT DOCUMENTS 6,872,195 B2 3/2005 Modak et al.
6,887,223 B2 5/2005 Bisbee
6,887,230 B2 5/2005 Kubalak et al.
6,889,740 B1 5/2005 Globensky et al.
6,918,924 B2 7/2005 Lasheras et al.
6,926,708 B1 8/2005 Franks-Farah et al.
6,939,339 B1 9/2005 Axexandersen et al.
6,939,554 B2 9/2005 McDonald et al.
6,941,171 B2 9/2005 Mann et al.
6,942,634 B2 9/2005 Odland
6,945,957 B2 9/2005 Freyman
6,949,598 B2 9/2005 Terry
6,951,902 B2 10/2005 McDonald et al.
6,972,040 B2 12/2005 Rioux et al.
7,001,370 B2 2/2006 Kubalak et al.
7,033,367 B2 4/2006 Ghahremani et al.
7,048,717 B1 5/2006 Frassica
7,059,330 B1 6/2006 Makower et al.
7,066,912 B2 6/2006 Nestenborg et al.
7,087,041 B2 8/2006 von Dyck et al.
7,087,048 B2 8/2006 Israelsson et al.
7,094,220 B2 8/2006 Tanghoj et al.
7,112,298 B2 9/2006 Kampa et al.
7,160,277 B2 1/2007 Elson et al.
7,166,092 B2 1/2007 Elson et al.
7,195,608 B2 3/2007 Burnett
7,204,940 B2 4/2007 McDonald et al.
7,211,275 B2 5/2007 Ying et al
7,244,242 B2 7/2007 Freyman
7,250,043 B2 7/2007 Chan et al.
7,255,687 B2 8/2007 Huang et al.
7,270,647 B2 9/2007 Karpowicz et al.
7,294,117 B2 11/2007 Provost-tine et al.
7,311,690 B2 12/2007 Burnett
7,311,698 B2 12/2007 Tanghoj et al.
7,329,412 B2 2/2008 Modak et al.
7,331,948 B2 2/2008 Skarda
7,334,679 B2 2/2008 Givens, Jr.
7,374,040 B2 5/2008 Lee et al.
7,380,658 B2 6/2008 Murray et al.
7,402,559 B2 7/2008 Catania et al.
7,445,812 B2 11/2008 Schmidt et al.
7,458,964 B2 12/2008 Mosler et al.
7,476,223 B2 1/2009 McBride
7,507,229 B2 3/2009 Hewitt et al.
7,517,343 B2 4/2009 Tanghoj et al.
7,537,589 B2 5/2009 Tsukada et al.
7,571,804 B2 8/2009 Kjellmann Bruun et al.
7,601,158 B2 10/2009 House
7,615,045 B2 11/2009 Israelsson et al.
7,628,784 B2 12/2009 Diaz et al.
7,632,256 B2 12/2009 Mosler et al.
D609,819 S 2/2010 Tomes et al.
7,662,146 B2 2/2010 House
7,670,331 B2 3/2010 Tanghoej
7,682,353 B2 3/2010 Tanghoj et al.
7,682,669 B1 3/2010 Michal et al.
7,691,091 B1 4/2010 Baggett
7,691,476 B2 4/2010 Finley
7,717,902 B2 5/2010 Sauer
7,749,529 B2 7/2010 Ash et al.
7,770,726 B2 8/2010 Murray et al.
7,770,728 B2 8/2010 Kaern
7,780,640 B1 8/2010 Amador
7,780,642 B2 8/2010 Rasmussen et al.
7,789,873 B2 9/2010 Kubalak et al.
7,820,734 B2 10/2010 McGhee
7,823,722 B2 11/2010 Bezou et al.
7,846,133 B2 12/2010 Windheuser et al.
7,867,220 B2 1/2011 Tanghoj
7,886,907 B2 2/2011 Murray et al.
7,896,857 B2 3/2011 Kay et al.
7,918,831 B2 4/2011 House
7,938,838 B2 5/2011 House
7,947,021 B2 5/2011 Bourne et al.
7,985,217 B2 7/2011 Mosler et al.
8,007,464 B2 8/2011 Gellman
8,011,505 B2 9/2011 Murray et al.
8,051,981 B2 11/2011 Murray et al.
8,052,673 B2 * 11/2011 Nestenborg ......... A61M 25/002
206/439
8,053,030 B2 11/2011 Gilman
8,066,693 B2 11/2011 Tanghoj et al.
8,127,922 B2 3/2012 Nordholm et al.
8,133,580 B2 3/2012 Dias et al.
8,163,327 B2 4/2012 Finley
8,177,774 B2 5/2012 House
8,181,778 B1 5/2012 van Groningen et al.
8,192,413 B2 6/2012 Bjerregaard
8,201,689 B2 6/2012 Kaern
8,205,745 B2 6/2012 Murray et al.
8,207,393 B2 6/2012 Bach
8,230,993 B2 7/2012 Tanghoej
8,267,919 B2 9/2012 Utas et al.
8,282,624 B2 10/2012 Tanghoej et al.
8,287,519 B2 10/2012 Smith
8,287,890 B2 10/2012 Elton
8,298,202 B2 10/2012 McCray
8,303,556 B2 11/2012 White
8,317,775 B2 11/2012 House
8,328,792 B2 12/2012 Nishtala et al.
8,356,457 B2 1/2013 Murray et al.
8,377,498 B2 2/2013 Rindlav-Westling et al.
8,377,559 B2 2/2013 Gilman
8,382,708 B2 2/2013 Mayback et al.
8,398,615 B2 3/2013 Torstensen et al.
8,409,171 B2 4/2013 Hannon et al.
8,454,569 B2 6/2013 Kull-Osterlin et al.
8,459,455 B2 6/2013 Frojd
8,475,434 B2 7/2013 Frojd
8,523,843 B2 9/2013 Kavanagh et al.
8,556,884 B2 10/2013 Hong et al.
8,608,718 B1 12/2013 Patterson-Young
8,668,683 B2 3/2014 Golden
8,720,685 B2 5/2014 Murray et al.
8,805,533 B2 8/2014 Boggs, II et al.
8,871,869 B2 10/2014 Dias et al.
8,888,747 B2 11/2014 House
8,919,553 B2 12/2014 Murray et al.
8,974,438 B2 3/2015 Hong et al.
8,998,882 B2 4/2015 Knapp et al.
9,033,149 B2 5/2015 Terry
9,072,862 B2 7/2015 Murray et al.
9,078,760 B2 7/2015 Marshall
9,108,020 B1 8/2015 Feloney
9,114,227 B2 8/2015 Blanchard
9,138,510 B2 9/2015 Madsen
9,144,659 B2 9/2015 Tanghoj
9,168,354 B2 10/2015 Hannon et al.
9,186,438 B2 11/2015 Gravesen et al.
9,192,506 B2 11/2015 Tanghoej et al.
9,192,740 B2 11/2015 Frojd
9,199,057 B2 12/2015 Nielsen
9,205,222 B2 12/2015 Tanghoj
9,220,866 B2 12/2015 Van Groningen et al.
9,289,575 B2 3/2016 Dye
9,314,585 B2 4/2016 Nestenborg et al.
9,345,855 B2 5/2016 Young
9,511,204 B2 12/2016 Tanghøj
9,561,889 B2 * 2/2017 Dayrit ................ B65D 75/5833
9,649,472 B2 5/2017 Kearns et al.
9,669,187 B2 6/2017 Tjassens et al.
9,687,628 B2 6/2017 Paz
9,694,113 B2 7/2017 Knapp et al.
9,694,157 B2 7/2017 Palmer
9,707,375 B2 7/2017 Conway et al.
9,731,093 B2 8/2017 Terry
9,775,965 B2 10/2017 Tanghoej et al.
9,801,979 B2 10/2017 Utas et al.
9,821,139 B2 11/2017 Carleo
9,872,969 B2 1/2018 Conway et al.
9,884,167 B2 2/2018 Gustavsson
9,918,869 B2 3/2018 Henry et al.
9,937,334 B2 4/2018 Fröjd et al.

(56) References Cited

U.S. PATENT DOCUMENTS 10,112,031 B2 10/2018 Matthiassen
10,118,019 B2 11/2018 Murray et al.
10,149,961 B2 12/2018 Carleo
10,166,366 B2 1/2019 Murray et al.
10,179,676 B1 1/2019 Taylor
10,207,076 B2 2/2019 Foley et al.
10,265,499 B2 4/2019 Hong et al.
10,328,237 B2 6/2019 Kelly et al.
10,406,322 B2 9/2019 O'Flynn et al.
10,441,454 B2 10/2019 Tanghoej et al.
10,449,328 B2 10/2019 Tanghoej et al.
10,449,329 B2 10/2019 Foley et al.
10,518,000 B2 12/2019 Knapp et al.
10,561,817 B2 2/2020 Hannon et al.
10,569,046 B2 * 2/2020 Steindahl ............ A61M 25/002
10,569,051 B2 2/2020 Conway et al.
10,639,451 B2 5/2020 Kearns et al.
10,646,688 B2 5/2020 Hannon et al.
10,702,671 B2 7/2020 Terry
10,758,704 B2 9/2020 Hickmott et al.
10,765,833 B2 9/2020 Kearns
10,857,324 B2 12/2020 Yin et al.
10,874,825 B2 12/2020 Yin et al.
RE48,426 E 2/2021 Murray et al.
10,912,917 B2 2/2021 Terry
11,020,561 B2 6/2021 O'Brien et al.
11,103,676 B2 8/2021 McMenamin et al.
11,129,961 B2 9/2021 O'Flynn
11,141,562 B2 10/2021 McMenamin et al.
11,154,688 B2 10/2021 Schertiger
11,167,107 B2 11/2021 Schertiger et al.
11,235,130 B2 2/2022 Murray et al.
11,241,566 B1 2/2022 Lindsay
11,253,675 B2 2/2022 Fletter
11,344,702 B2 5/2022 Subramaniam et al.
11,400,257 B2 8/2022 Tierney et al.
11,420,017 B2 8/2022 Hilton et al.
11,534,573 B2 12/2022 Hannon et al.
11,547,833 B2 1/2023 Murray et al.
11,607,524 B2 3/2023 Conway et al.
11,660,385 B1 * 5/2023 Thakore ................ B65D 65/22
206/364
12,076,506 B2 * 9/2024 Palmer .............. A61M 25/0113
12,383,700 B2 8/2025 Murray et al.
2001/0001443 A1 5/2001 Kayerod et al.
2001/0027299 A1 10/2001 Yang et al.
2001/0031933 A1 10/2001 Cannon
2001/0031952 A1 10/2001 Karram et al.
2001/0047147 A1 11/2001 Slepian et al.
2001/0054562 A1 12/2001 Pettersson et al.
2002/0007175 A1 1/2002 Chang
2002/0032406 A1 3/2002 Kusleika
2002/0037943 A1 3/2002 Madsen
2002/0045855 A1 4/2002 Frassica
2002/0055730 A1 5/2002 Yachia et al.
2002/0077611 A1 6/2002 von Dyck et al.
2002/0082551 A1 6/2002 Yachia et al.
2002/0087131 A1 7/2002 Wolff et al.
2002/0094322 A1 7/2002 Lawson et al.
2002/0095133 A1 7/2002 Gillis et al.
2002/0099356 A1 7/2002 Unger et al.
2002/0103467 A1 8/2002 Kubalak
2002/0107467 A1 8/2002 Levin
2002/0132013 A1 9/2002 Moulis
2002/0132049 A1 9/2002 Leonard et al.
2002/0133130 A1 9/2002 Wilcox
2002/0156440 A1 10/2002 Israelsson et al.
2002/0165427 A1 11/2002 Yachia et al.
2002/0169438 A1 11/2002 Sauer
2002/0182265 A1 12/2002 Burrell et al.
2003/0004496 A1 1/2003 Tanghoj
2003/0018293 A1 1/2003 Tanghoj et al.
2003/0018302 A1 1/2003 Kavanagh et al.
2003/0018322 A1 1/2003 Tanghoj et al.
2003/0023222 A1 1/2003 Chen
2003/0028174 A1 2/2003 Chan et al.
2003/0036802 A1 2/2003 Lennox et al.
2003/0055403 A1 3/2003 Nestenborg et al.
2003/0060807 A1 3/2003 Tanghoj et al.
2003/0065292 A1 4/2003 Darouiche et al.
2003/0083644 A1 5/2003 Avaltroni
2003/0130646 A1 7/2003 Kubalak et al.
2003/0132307 A1 7/2003 Park
2003/0135200 A1 7/2003 Byrne
2003/0163079 A1 8/2003 Burnett
2003/0168365 A1 * 9/2003 Kaern ................ A61M 25/002
206/466
2003/0195478 A1 10/2003 Russo
2003/0225392 A1 12/2003 McMichael et al.
2003/0233084 A1 12/2003 Slepian et al.
2004/0030301 A1 2/2004 Hunter
2004/0034329 A1 2/2004 Mankus et al.
2004/0044307 A1 3/2004 Richardson et al.
2004/0049152 A1 3/2004 Nayak
2004/0049170 A1 3/2004 Snell
2004/0055925 A1 3/2004 Franks-Farah et al.
2004/0059280 A1 3/2004 Makower et al.
2004/0068251 A1 4/2004 Chan et al.
2004/0074794 A1 4/2004 Conway et al.
2004/0097892 A1 5/2004 Evans et al.
2004/0116551 A1 6/2004 Terry
2004/0122382 A1 6/2004 Johnson et al.
2004/0127848 A1 7/2004 Freyman
2004/0133156 A1 7/2004 Diaz et al.
2004/0147871 A1 7/2004 Burnett
2004/0153049 A1 8/2004 Hewitt et al.
2004/0153051 A1 8/2004 Israelsson et al.
2004/0158231 A1 8/2004 Tanghoj et al.
2004/0163980 A1 8/2004 Tanghoj et al.
2004/0176747 A1 9/2004 Feneley
2004/0193143 A1 9/2004 Sauer
2004/0234572 A1 11/2004 Martinod et al.
2004/0236293 A1 11/2004 Tanghoj et al.
2004/0243104 A1 12/2004 Seddon
2004/0249343 A1 12/2004 Cioanta
2004/0254562 A1 12/2004 Tanghoj et al.
2004/0256264 A1 12/2004 Israelsson et al.
2005/0003118 A1 1/2005 Takala
2005/0011790 A1 1/2005 Harrold
2005/0015076 A1 1/2005 Giebmeyer et al.
2005/0031872 A1 2/2005 Schmidt et al.
2005/0033222 A1 2/2005 Haggstrom et al.
2005/0043715 A1 2/2005 Nestenborg et al.
2005/0049577 A1 3/2005 Snell et al.
2005/0059990 A1 3/2005 Ayala et al.
2005/0065499 A1 3/2005 Douk et al.
2005/0070882 A1 3/2005 McBride
2005/0080399 A1 4/2005 Bolmsjo et al.
2005/0096582 A1 5/2005 Burnett
2005/0101923 A1 5/2005 Elson et al.
2005/0101924 A1 5/2005 Elson et al.
2005/0107735 A1 5/2005 Lennox et al.
2005/0107771 A1 5/2005 Finkbeiner
2005/0109648 A1 5/2005 Kerzman et al.
2005/0137522 A1 6/2005 Aoki
2005/0137582 A1 6/2005 Kull-Osterlin et al.
2005/0143690 A1 6/2005 High
2005/0148950 A1 7/2005 Windheuser et al.
2005/0177104 A1 8/2005 Conway
2005/0197531 A1 9/2005 Cabiri et al.
2005/0199521 A1 9/2005 Givens
2005/0209580 A1 9/2005 Freyman
2005/0214443 A1 9/2005 Madsen
2005/0245901 A1 11/2005 Floyd
2005/0251108 A1 11/2005 Frassica
2005/0256447 A1 11/2005 Richardson et al.
2005/0273034 A1 12/2005 Burnett
2005/0282977 A1 12/2005 Stempel et al.
2005/0283136 A1 12/2005 Skarda
2006/0025753 A1 2/2006 Kubalak et al.
2006/0027854 A1 2/2006 Kim et al.
2006/0030864 A1 2/2006 Kennedy et al.
2006/0036208 A1 2/2006 Burnett
2006/0041246 A1 2/2006 Provost-tine et al.

(56) References Cited

U.S. PATENT DOCUMENTS

2006/0054557 A1 3/2006 Hori et al.
2006/0058777 A1 3/2006 Nielsen
2006/0064065 A1 3/2006 Russo
2006/0079835 A1 4/2006 Frassica
2006/0079854 A1 4/2006 Kay et al.
2006/0100511 A1 5/2006 Eriksen
2006/0122566 A1 6/2006 Huang et al.
2006/0122568 A1 6/2006 Elson et al.
2006/0142737 A1 6/2006 Tanghoj
2006/0172096 A1 8/2006 Kyle et al.
2006/0184112 A1 8/2006 Horn et al.
2006/0184145 A1 8/2006 Ciok et al.
2006/0189962 A1 8/2006 Burtoft
2006/0196783 A1 9/2006 Bruun et al.
2006/0200079 A1 9/2006 Magnusson
2006/0229576 A1 10/2006 Conway et al.
2006/0240069 A1 10/2006 Utas et al.
2006/0263404 A1 11/2006 Nielsen et al.
2006/0271019 A1 11/2006 Stoller et al.
2006/0276894 A1 12/2006 Finley
2006/0278546 A1 12/2006 State et al.
2006/0293642 A1 12/2006 Israelsson et al.
2007/0005024 A1 1/2007 Weber et al.
2007/0005041 A1 1/2007 Frassica et al.
2007/0010798 A1 1/2007 Stoller et al.
2007/0016168 A1 1/2007 Conway
2007/0016169 A1 1/2007 Utas et al.
2007/0049879 A1 3/2007 Gutierrez
2007/0059350 A1 3/2007 Kennedy et al.
2007/0066963 A1 3/2007 Tanghoj
2007/0084749 A1 4/2007 Demelo et al.
2007/0088330 A1 4/2007 House
2007/0106233 A1 5/2007 Huang et al.
2007/0108076 A1 5/2007 Miller et al.
2007/0112327 A1 5/2007 Yun et al.
2007/0112333 A1 5/2007 Hoang et al.
2007/0149929 A1 6/2007 Utas et al.
2007/0161971 A1 7/2007 House
2007/0197957 A1 8/2007 Hunter et al.
2007/0218102 A1 9/2007 Chudzik et al.
2007/0225635 A1 9/2007 Lynn
2007/0225649 A1 9/2007 House
2007/0225687 A1 9/2007 House
2007/0244449 A1 10/2007 Najafi et al.
2007/0287800 A1 12/2007 Acquarulo et al.
2007/0289887 A1* 12/2007 Murray .................. B65D 51/00 53/396
2008/0006554 A1 1/2008 Duffy et al.
2008/0015518 A1 1/2008 Huang et al.
2008/0015527 A1 1/2008 House
2008/0021382 A1 1/2008 Freyman
2008/0027414 A1 1/2008 Tanghoj et al.
2008/0033471 A1 2/2008 Paz et al.
2008/0050446 A1 2/2008 Ziegler et al.
2008/0051762 A1 2/2008 Tsukada et al.
2008/0051763 A1 2/2008 Frojd
2008/0063324 A1* 3/2008 Bernard ............. B65D 75/5811 383/200
2008/0077099 A1 3/2008 House
2008/0082051 A1 4/2008 Miller et al.
2008/0085949 A1 4/2008 McGhee
2008/0086008 A1 4/2008 Lhermitte et al.
2008/0091145 A1 4/2008 House
2008/0097362 A1 4/2008 Mosler et al.
2008/0097394 A1 4/2008 Lampropoulos et al.
2008/0097411 A1 4/2008 House
2008/0103464 A1 5/2008 Mosler et al.
2008/0119803 A1 5/2008 Lund
2008/0125513 A1 5/2008 Kristiansen
2008/0140010 A1 6/2008 Kennedy et al.
2008/0140052 A1 6/2008 Moller et al.
2008/0171973 A1 7/2008 House
2008/0171998 A1 7/2008 House
2008/0172016 A1 7/2008 House
2008/0172040 A1 7/2008 Smith
2008/0172042 A1 7/2008 House
2008/0177217 A1 7/2008 Polaschegg
2008/0179208 A1 7/2008 Murray et al.
2008/0183262 A1 7/2008 Dowling
2008/0193497 A1 8/2008 Samuelsen et al.
2008/0200907 A1 8/2008 Nestenborg
2008/0215021 A1 9/2008 Cisko, Jr. et al.
2008/0243081 A1 10/2008 Nance et al.
2008/0243091 A1 10/2008 Humphreys et al.
2008/0249467 A1 10/2008 Burnett et al.
2008/0249482 A1 10/2008 Erez
2008/0275463 A1 11/2008 High
2008/0279907 A1 11/2008 Ash et al.
2008/0281291 A1 11/2008 Tihon et al.
2009/0000970 A1 1/2009 Bordeau et al.
2009/0005725 A1 1/2009 Shorey
2009/0012208 A1 1/2009 Madsen et al.
2009/0024111 A1 1/2009 Borodulin et al.
2009/0043287 A1 2/2009 Mosler et al.
2009/0048537 A1 2/2009 Lydon et al.
2009/0048570 A1 2/2009 Jensen
2009/0054876 A1 2/2009 Borodulin et al.
2009/0062754 A1 3/2009 Tang
2009/0065605 A1 3/2009 Roche et al.
2009/0071851 A1 3/2009 Maki et al.
2009/0099532 A1 4/2009 Cuevas et al.
2009/0101531 A1 4/2009 Nordholm et al.
2009/0112171 A1 4/2009 Ng et al.
2009/0131917 A1 5/2009 Kavanagh et al.
2009/0137985 A1 5/2009 Tanghoej et al.
2009/0137986 A1 5/2009 Golden et al.
2009/0149837 A1 6/2009 Tanghoj et al.
2009/0156882 A1 6/2009 Chi Sing et al.
2009/0163884 A1 6/2009 Kull-Osterlin et al.
2009/0200187 A1 8/2009 Nestenborg et al.
2009/0208368 A1 8/2009 Waldrep et al.
2009/0221992 A1 9/2009 Hannon et al.
2009/0299334 A1 12/2009 Nishtala et al.
2009/0314795 A1 12/2009 Rapko et al.
2009/0318900 A1 12/2009 Tanghoj et al.
2010/0010086 A1 1/2010 Ash et al.
2010/0030197 A1 2/2010 House
2010/0036363 A1 2/2010 Watanabe et al.
2010/0047123 A1 2/2010 Solomon et al.
2010/0086580 A1 4/2010 Nyman et al.
2010/0133172 A1 6/2010 Song et al.
2010/0152686 A1 6/2010 Ryder et al.
2010/0155268 A1 6/2010 Murray et al.
2010/0198195 A1 8/2010 Nishtala et al.
2010/0228233 A1 9/2010 Kahn
2010/0256576 A1 10/2010 Aggarwal et al.
2010/0258568 A1 10/2010 Frederiksen et al.
2010/0263327 A1 10/2010 Murray et al.
2010/0324540 A1 12/2010 Paulen et al.
2011/0028943 A1 2/2011 Lawson et al.
2011/0056852 A1 3/2011 Frojd
2011/0059874 A1 3/2011 Rooijmans et al.
2011/0060317 A1 3/2011 Frojd
2011/0114520 A1 5/2011 Matthison-Hansen
2011/0127186 A1 6/2011 Enns et al.
2011/0137243 A1 6/2011 Hossainy et al.
2011/0137296 A1 6/2011 Tanghoj
2011/0144579 A1 6/2011 Elton
2011/0147238 A1 6/2011 Tanghoej et al.
2011/0152843 A1 6/2011 Wedlin et al.
2011/0160704 A1 6/2011 Park
2011/0178507 A1 7/2011 Bracken et al.
2011/0184386 A1 7/2011 House
2011/0213025 A1 9/2011 Finch, Jr.
2011/0224653 A1 9/2011 Torstensen
2011/0284409 A1 11/2011 Murray et al.
2011/0295239 A1 12/2011 Gustavsson
2012/0037525 A1 2/2012 Peck et al.
2012/0168324 A1 7/2012 Carleo
2012/0179102 A1 7/2012 Blanchard et al.
2012/0179144 A1 7/2012 Carleo
2012/0193255 A1 8/2012 Lareau et al.
2012/0219742 A1 8/2012 Gravesen et al.
2012/0228165 A1 9/2012 Murray et al.

(56) References Cited

U.S. PATENT DOCUMENTS

2012/0239005 A1 9/2012 Conway et al.
2012/0271101 A1 10/2012 Tan
2012/0284991 A1 11/2012 Kusz et al.
2012/0308805 A1 12/2012 Sella
2012/0310210 A1 12/2012 Campbell et al.
2012/0316515 A1 12/2012 Terry
2012/0330255 A1 12/2012 Carlin
2013/0006226 A1 1/2013 Hong et al.
2013/0037306 A1 2/2013 Kim
2013/0048516 A1 2/2013 Nishtala et al.
2013/0077899 A1* 3/2013 Odabashian ....... B65D 75/5833 383/205
2013/0085469 A1 4/2013 Polaschegg
2013/0131647 A1 5/2013 Nielsen
2013/0138083 A1 5/2013 Tennican
2013/0138088 A1 5/2013 Nielsen
2013/0146599 A1 6/2013 Murray et al.
2013/0153446 A1 6/2013 Utas et al.
2013/0161208 A1 6/2013 Gustavsson
2013/0161227 A1 6/2013 Gustavsson
2013/0186778 A1 7/2013 Terry
2013/0218136 A1 8/2013 Tanghoej et al.
2013/0231641 A1 9/2013 Gustavsson
2013/0253426 A1 9/2013 Campbell et al.
2013/0261608 A1 10/2013 Tanghoj
2013/0264227 A1 10/2013 Frojd
2013/0289537 A1 10/2013 Schertiger et al.
2014/0066904 A1 3/2014 Young
2014/0066905 A1 3/2014 Young
2014/0193474 A1 7/2014 Babcock et al.
2014/0194857 A1 7/2014 Eilat
2014/0224678 A1 8/2014 Schertiger et al.
2014/0262859 A1 9/2014 Knapp et al.
2014/0271351 A1 9/2014 Nielsen et al.
2014/0271400 A1 9/2014 Cheng et al.
2014/0287172 A1* 9/2014 Finley ................ B65D 75/5827 428/34.9
2015/0001107 A1 1/2015 Gustavsson
2015/0018962 A1 1/2015 Matsumoto et al.
2015/0051587 A1 2/2015 Rolsted et al.
2015/0068927 A1 3/2015 McBurney et al.
2015/0105756 A1 4/2015 O'Brien et al.
2015/0126975 A1 5/2015 Wuthier
2015/0132468 A1 5/2015 Cage et al.
2015/0133898 A1 5/2015 Murray et al.
2015/0202405 A1 7/2015 Schertiger et al.
2015/0231377 A1 8/2015 Tierney et al.
2015/0238726 A1 8/2015 Terry
2015/0258305 A1 9/2015 Dye
2015/0265801 A1 9/2015 Rostami
2015/0273116 A1 10/2015 Knapp et al.
2015/0273183 A1 10/2015 Foley et al.
2015/0297861 A1 10/2015 Passalaqua et al.
2015/0297862 A1 10/2015 Sadik et al.
2015/0306342 A1 10/2015 Rostami et al.
2015/0314103 A1 11/2015 Hannon et al.
2015/0335823 A1 11/2015 Weikart et al.
2015/0335854 A1 11/2015 Dvarsater et al.
2015/0335856 A1 11/2015 Utas et al.
2015/0335872 A1 11/2015 Yang et al.
2015/0343171 A1 12/2015 Hannon
2015/0352324 A1 12/2015 Palmer
2015/0359996 A1 12/2015 Arora et al.
2016/0001037 A1 1/2016 Hong et al.
2016/0038652 A1 2/2016 Gilman
2016/0038713 A1 2/2016 Kearns et al.
2016/0120688 A1 5/2016 Lee
2016/0166822 A1 6/2016 Dodson et al.
2016/0175488 A1 6/2016 Klein et al.
2016/0184551 A1 6/2016 Nyman et al.
2016/0193447 A1 7/2016 Matthiassen
2016/0220784 A1 8/2016 Palmer
2016/0317715 A1 11/2016 Rostami et al.
2016/0325088 A1 11/2016 Nordquist et al.
2016/0325089 A1 11/2016 Burkholz
2017/0173300 A1 6/2017 Hannon et al.
2017/0217658 A1 8/2017 Whitehurst
2017/0296704 A1 10/2017 Knapp et al.
2017/0326334 A1 11/2017 Terry
2018/0021481 A1 1/2018 Yin et al.
2018/0050173 A1 2/2018 Kearns
2018/0071486 A1 3/2018 O'Flynn
2018/0104444 A1 4/2018 Yin et al.
2018/0110961 A1 4/2018 Steindahl et al.
2018/0163152 A1 6/2018 Luo et al.
2018/0169377 A1 6/2018 Hickmott et al.
2019/0047766 A1 2/2019 Brooks et al.
2019/0083746 A1 3/2019 Murray et al.
2019/0105462 A1 4/2019 Schertiger
2019/0110879 A1 4/2019 Camp et al.
2019/0126004 A1 5/2019 O'Brien et al.
2019/0151605 A1 5/2019 McMenamin et al.
2019/0151610 A1 5/2019 Fletter
2019/0216985 A1 7/2019 Mcburney et al.
2019/0255280 A1 8/2019 Palmer
2019/0321593 A1 10/2019 Crawford
2019/0358435 A1 11/2019 Andersin et al.
2019/0381272 A1 12/2019 Terry
2020/0001043 A1 1/2020 Heneghan et al.
2020/0016380 A1 1/2020 Murray et al.
2020/0031550 A1* 1/2020 Douglas ............. B65D 75/5827
2020/0115102 A1 4/2020 Hawry
2020/0155261 A1* 5/2020 O'Flynn .............. B65D 75/326
2020/0155794 A1 5/2020 Ziebol
2020/0155796 A1 5/2020 Hannon et al.
2020/0171218 A1 6/2020 Dong et al.
2020/0179647 A1 6/2020 Conway et al.
2020/0188631 A1 6/2020 Hannon et al.
2020/0222659 A1 7/2020 Schertiger et al.
2020/0230349 A1 7/2020 McMenamin et al.
2020/0238048 A1* 7/2020 Palmer ................ B65D 75/585
2020/0246594 A1 8/2020 Miller
2020/0281751 A1 9/2020 Schreck et al.
2020/0282177 A1 9/2020 Farrell
2020/0345977 A1 11/2020 Hickmott et al.
2020/0361076 A1 11/2020 Richart
2020/0383822 A1 12/2020 Palmer
2020/0391005 A1 12/2020 Murray et al.
2020/0398023 A1 12/2020 Conway et al.
2020/0398024 A1 12/2020 Fletter et al.
2021/0008361 A1 1/2021 Aronson
2021/0100979 A1 4/2021 Donnelly et al.
2021/0113808 A1 4/2021 Yin et al.
2021/0187238 A1 6/2021 O'Brien et al.
2021/0212808 A1 7/2021 Wu et al.
2021/0283367 A1 9/2021 Peters
2021/0290894 A1 9/2021 Palmer
2021/0290895 A1 9/2021 Nielsen et al.
2021/0402135 A1 12/2021 McMenamin et al.
2022/0023585 A1 1/2022 Schertiger et al.
2022/0054295 A1 2/2022 Becker
2022/0112018 A1* 4/2022 Montano ................ B65D 65/40
2022/0117850 A1 4/2022 Romeo et al.
2022/0142810 A1 5/2022 Whittaker
2022/0241549 A1 8/2022 Murray et al.
2022/0273837 A1 9/2022 Paul et al.
2022/0362536 A1 11/2022 Nguyen et al.
2023/0058911 A1 2/2023 Nabors et al.
2023/0072221 A1 3/2023 Donnelly et al.
2023/0073264 A1 3/2023 Kandrac et al.
2023/0075906 A1 3/2023 Piashevich et al.
2023/0077075 A1 3/2023 Kandrac et al.
2023/0166073 A1 6/2023 Radmer
2023/0293848 A1 9/2023 Legaspi et al.
2023/0293849 A1 9/2023 Hughett, Sr. et al.
2023/0364379 A1 11/2023 Hughett, Sr. et al.
2024/0108850 A1 4/2024 Yin et al.
2024/0269426 A1 8/2024 Siddiqui
2024/0325685 A1 10/2024 Daw et al.
2024/0342332 A1* 10/2024 Paras ........................ A61L 2/23
2025/0082897 A1* 3/2025 Pfleger .................. A61M 39/24
2025/0114231 A1 4/2025 Legaspi et al.

(56) References Cited

U.S. PATENT DOCUMENTS

| | | | |
|---|---|---|---|
| 2025/0288774 | A1 | 9/2025 | Kulkarni et al. |
| 2025/0325785 | A1 | 10/2025 | Kulkarni et al. |

FOREIGN PATENT DOCUMENTS

| | | | |
|---|---|---|---|
| AU | 2022354188 | A1 | 3/2024 |
| BR | PI0803737 | A2 | 1/2010 |
| CA | 763930 | A | 7/1967 |
| CA | 2770300 | A1 | 2/2011 |
| CA | 2769026 | C | 4/2015 |
| CA | 3083014 | A1 | 5/2019 |
| CN | 1106744 | A | 8/1995 |
| CN | 2532840 | Y | 1/2003 |
| CN | 2907580 | Y | 6/2007 |
| CN | 101035573 | A | 9/2007 |
| CN | 101365501 | A | 2/2009 |
| CN | 102939127 | A | 2/2013 |
| CN | 102939129 | A | 2/2013 |
| CN | 102973986 | A | 3/2013 |
| CN | 102973987 | A | 3/2013 |
| CN | 107088243 | A | 8/2017 |
| CN | 111870742 | A | 11/2020 |
| CN | 217015042 | U | 7/2022 |
| CN | 116056746 | A | 5/2023 |
| DE | 352014 | C | 4/1922 |
| DE | 1913976 | U | 4/1965 |
| DE | 4135502 | C1 | 2/1993 |
| DE | 4303899 | A1 | 8/1994 |
| DE | 19826746 | C1 | 11/1999 |
| DE | 10038521 | A1 | 2/2002 |
| DE | 10213411 | A1 | 10/2003 |
| DE | 10259002 | A1 | 10/2003 |
| DE | 10334372 | A1 | 2/2005 |
| DE | 202005009946 | U1 | 9/2005 |
| DE | 202005009947 | U1 | 9/2005 |
| DE | 102007018275 | A1 | 3/2008 |
| DE | 102009025347 | A1 | 12/2010 |
| DE | 202012000538 | U1 | 3/2012 |
| DE | 202011107059 | U1 | 1/2013 |
| DE | 202013002466 | U1 | 3/2013 |
| DE | 102011085864 | A1 | 5/2013 |
| DE | 102012000844 | A1 | 7/2013 |
| DE | 102016120294 | A1 | 4/2018 |
| DE | 112018000170 | T5 | 10/2019 |
| EP | 0055023 | A2 | 6/1982 |
| EP | 0182409 | A1 | 5/1986 |
| EP | 0184629 | A2 | 6/1986 |
| EP | 0187846 | A1 | 7/1986 |
| EP | 0193406 | A2 | 9/1986 |
| EP | 0218203 | A1 | 4/1987 |
| EP | 0236458 | A1 | 9/1987 |
| EP | 247559 | A1 | 12/1987 |
| EP | 0252918 | A1 | 1/1988 |
| EP | 0298634 | A1 | 1/1989 |
| EP | 0303487 | A2 | 2/1989 |
| EP | 0335564 | A1 | 10/1989 |
| EP | 0352043 | A1 | 1/1990 |
| EP | 0390720 | A1 | 10/1990 |
| EP | 0407218 | A1 | 1/1991 |
| EP | 0217771 | B1 | 12/1991 |
| EP | 0471553 | A1 | 2/1992 |
| EP | 0479935 | A1 | 4/1992 |
| EP | 0528965 | A1 | 3/1993 |
| EP | 0553960 | A1 | 8/1993 |
| EP | 0590104 | A1 | 4/1994 |
| EP | 0598191 | A1 | 5/1994 |
| EP | 0663196 | A1 | 7/1995 |
| EP | 0677299 | A1 | 10/1995 |
| EP | 0680895 | A1 | 11/1995 |
| EP | 0685179 | A1 | 12/1995 |
| EP | 0699086 | A1 | 3/1996 |
| EP | 0767639 | A1 | 4/1997 |
| EP | 0768069 | A1 | 4/1997 |
| EP | 0795339 | A1 | 9/1997 |
| EP | 0815037 | A1 | 1/1998 |
| EP | 0909249 | A1 | 4/1999 |
| EP | 0923398 | A1 | 6/1999 |
| EP | 0935478 | A1 | 8/1999 |
| EP | 0959930 | A1 | 12/1999 |
| EP | 0977610 | A2 | 2/2000 |
| EP | 1018323 | A1 | 7/2000 |
| EP | 1023882 | A1 | 8/2000 |
| EP | 1047360 | A1 | 11/2000 |
| EP | 1115450 | A1 | 7/2001 |
| EP | 1131022 | A1 | 9/2001 |
| EP | 1175355 | A1 | 1/2002 |
| EP | 1237615 | A1 | 9/2002 |
| EP | 1245205 | A2 | 10/2002 |
| EP | 1308146 | A1 | 5/2003 |
| EP | 1321163 | A1 | 6/2003 |
| EP | 1347723 | A1 | 10/2003 |
| EP | 1406690 | A2 | 4/2004 |
| EP | 1409060 | A2 | 4/2004 |
| EP | 1090656 | B1 | 5/2004 |
| EP | 1420846 | A1 | 5/2004 |
| EP | 1420847 | A2 | 5/2004 |
| EP | 1427467 | A2 | 6/2004 |
| EP | 1485158 | A2 | 12/2004 |
| EP | 1498151 | A2 | 1/2005 |
| EP | 1567219 | A1 | 8/2005 |
| EP | 1578308 | A1 | 9/2005 |
| EP | 1145729 | B1 | 11/2005 |
| EP | 1606196 | A2 | 12/2005 |
| EP | 1615690 | A1 | 1/2006 |
| EP | 1629799 | A1 | 3/2006 |
| EP | 1629860 | | 3/2006 |
| EP | 1641510 | A1 | 4/2006 |
| EP | 1642610 | | 4/2006 |
| EP | 1642611 | | 4/2006 |
| EP | 1695678 | A1 | 8/2006 |
| EP | 1357868 | B1 | 9/2006 |
| EP | 1723980 | A2 | 11/2006 |
| EP | 1744803 | A2 | 1/2007 |
| EP | 1757251 | A2 | 2/2007 |
| EP | 1788990 | A1 | 5/2007 |
| EP | 1793938 | A1 | 6/2007 |
| EP | 1799163 | A1 | 6/2007 |
| EP | 1824534 | A2 | 8/2007 |
| EP | 1824549 | A2 | 8/2007 |
| EP | 1858575 | A1 | 11/2007 |
| EP | 1904003 | A2 | 4/2008 |
| EP | 1948279 | A1 | 7/2008 |
| EP | 1955683 | A1 | 8/2008 |
| EP | 2060296 | A1 | 5/2009 |
| EP | 2106821 | A1 | 10/2009 |
| EP | 2275058 | A1 | 1/2011 |
| EP | 2292293 | A1 | 3/2011 |
| EP | 2292294 | A1 | 3/2011 |
| EP | 2308542 | A1 | 4/2011 |
| EP | 2423125 | A1 | 2/2012 |
| EP | 2423126 | A1 | 2/2012 |
| EP | 2423127 | A1 | 2/2012 |
| EP | 2450076 | A1 | 5/2012 |
| EP | 2459264 | A1 | 6/2012 |
| EP | 2464411 | A1 | 6/2012 |
| EP | 2468347 | A1 | 6/2012 |
| EP | 2500056 | A2 | 9/2012 |
| EP | 1786501 | B1 | 11/2012 |
| EP | 2542291 | A1 | 1/2013 |
| EP | 1578468 | B1 | 4/2013 |
| EP | 2574354 | A1 | 4/2013 |
| EP | 2424470 | B1 | 8/2013 |
| EP | 2504054 | B1 | 9/2013 |
| EP | 2644224 | A3 | 3/2014 |
| EP | 1962937 | B1 | 8/2014 |
| EP | 2774648 | A1 | 9/2014 |
| EP | 2515985 | B1 | 12/2014 |
| EP | 2686054 | B1 | 12/2014 |
| EP | 2908897 | A1 | 8/2015 |
| EP | 2898918 | A3 | 9/2015 |
| EP | 2914222 | A1 | 9/2015 |
| EP | 2967968 | A1 | 1/2016 |
| EP | 1852139 | B1 | 5/2016 |
| EP | 2515988 | B1 | 7/2016 |

(56) References Cited

FOREIGN PATENT DOCUMENTS

EP 2777747 B1 5/2017
EP 3199130 A1 8/2017
EP 3231471 A1 10/2017
EP 3078393 B1 11/2017
EP 3272385 A1 1/2018
EP 3222316 B1 5/2018
EP 3352831 A1 8/2018
EP 2782629 B1 4/2019
EP 3313494 B1 5/2019
EP 3478353 A1 5/2019
EP 2826514 B1 6/2019
EP 3490654 A1 6/2019
EP 2946803 B1 7/2019
EP 3551103 A1 10/2019
EP 3566739 A1 11/2019
EP 3570925 A1 11/2019
EP 3092024 B1 12/2019
EP 3583972 A2 12/2019
EP 3388103 B1 1/2020
EP 3590573 A1 1/2020
EP 3079752 B1 4/2020
EP 3100758 B1 4/2020
EP 2826515 B1 5/2020
EP 3079748 B1 5/2020
EP 3651844 A1 5/2020
EP 2651485 B1 6/2020
EP 3038690 B1 7/2020
EP 3119464 B1 9/2020
EP 3132823 B1 9/2020
EP 3299056 B1 9/2020
EP 3701993 A1 9/2020
EP 3709940 A1 9/2020
EP 3710095 A1 9/2020
EP 3711806 A1 9/2020
EP 3711807 A1 9/2020
EP 3711808 A1 9/2020
EP 3713632 A2 9/2020
EP 3392167 B1 10/2020
EP 2468346 B1 11/2020
EP 3077031 B1 11/2020
EP 3738640 A1 11/2020
EP 3769803 A2 1/2021
EP 2995268 B1 3/2021
EP 3793627 A1 3/2021
EP 2968833 B1 5/2021
EP 3952973 A1 2/2022
EP 3082929 B1 3/2022
EP 3310421 B1 3/2022
EP 3725355 B1 5/2022
EP 2688629 B1 12/2022
ES 2645658 B1 10/2018
FR 1558162 A 2/1969
FR 96086 E 5/1972
FR 2127704 A5 10/1972
FR 2351634 A1 12/1977
FR 2731345 A1 9/1996
FR 2794638 A1 12/2000
FR 2855399 A1 12/2004
FR 3042716 B1 10/2021
GB 322426 A 12/1929
GB 1131865 A 10/1968
GB 2007507 A 5/1979
GB 2106784 A 4/1983
GB 2150938 A 7/1985
GB 2187670 A 9/1987
GB 2231801 A 11/1990
GB 2239804 A 7/1991
GB 2319507 5/1998
GB 2284764 B 8/1998
GB 2427362 B 9/2008
GB 2462267 A 2/2010
GB 2469824 B 8/2011
GB 2532459 B 12/2016
GB 2565585 A 2/2019
GB 2561843 B 9/2021
JP S5512265 B2 3/1980
JP S59218157 A 12/1984
JP S59228856 A 12/1984
JP H09206370 A 8/1997
JP H10151094 A 6/1998
JP H10277144 A 10/1998
JP 2001500414 A 1/2001
JP 200150329 A 2/2001
JP 2002530148 A 9/2002
JP 2002282275 A 10/2002
JP 2002543885 A 12/2002
JP 2007501656 A 2/2007
JP 2007167158 A 7/2007
JP 200851549 A 3/2008
JP 2008508077 A 3/2008
JP 2008526377 A 7/2008
JP 2009125583 A 6/2009
JP 2010538106 A 12/2010
JP 2011510110 A 3/2011
JP 2013500125 A 1/2013
JP 2013515572 5/2013
KR 1020160035437 A 3/2016
RU 2009105497 A 8/2010
WO 1984001102 A1 3/1984
WO 198401296 A1 4/1984
WO 1986000816 A1 2/1986
WO 1986006284 A1 11/1986
WO 1987001582 A1 3/1987
WO 1989003232 A1 4/1989
WO 1989009626 A1 10/1989
WO 1990004431 A1 5/1990
WO 1991005577 A1 5/1991
WO 1991010466 A1 7/1991
WO 1991017728 A1 11/1991
WO 9208426 A1 5/1992
WO 1992010220 A1 6/1992
WO 1992011826 A1 7/1992
WO 1992019192 A1 11/1992
WO 1993000054 A1 1/1993
WO 9311821 A1 6/1993
WO 9314806 A1 8/1993
WO 1994006377 A1 3/1994
WO 1994016747 A1 8/1994
WO 1994026215 A1 11/1994
WO 1995008968 A1 4/1995
WO 1995009667 A1 4/1995
WO 1995017862 A1 7/1995
WO 1995034253 A1 12/1995
WO 1996000541 A1 1/1996
WO 1996004119 A1 2/1996
WO 9607447 A1 3/1996
WO 1996019254 A1 6/1996
WO 1996026688 A1 9/1996
WO 1996030277 A1 10/1996
WO 1996034587 A1 11/1996
WO 9641653 A1 12/1996
WO 1996038192 A1 12/1996
WO 1996039096 A1 12/1996
WO 1997025947 A1 7/1997
WO 1997026937 A1 7/1997
WO 1997041811 A1 11/1997
WO 1998006642 A1 2/1998
WO 1998011932 3/1998
WO 1998019729 5/1998
WO 9846176 A1 10/1998
WO 1999007313 A1 2/1999
WO 1999030761 A1 6/1999
WO 1999036009 A1 7/1999
WO 2000016843 3/2000
WO 2000025848 A2 5/2000
WO 0030696 A1 6/2000
WO 2000030575 A1 6/2000
WO 2000047494 A1 8/2000
WO 2001043807 A1 6/2001
WO 2001052763 A1 7/2001
WO 2001093935 A1 12/2001
WO 2002036192 A1 5/2002
WO 2002053070 A1 7/2002
WO 2002060361 A2 8/2002

(56) References Cited

FOREIGN PATENT DOCUMENTS

WO 03008028 A2 1/2003
WO 2003002177 1/2003
WO 2003002178 A2 1/2003
WO 2003008029 1/2003
WO 2003022333 A1 3/2003
WO 2003064279 A1 8/2003
WO 03092779 A1 11/2003
WO 03093357 A1 11/2003
WO 2004004611 A1 1/2004
WO 2004004796 A1 1/2004
WO 2004030722 A2 4/2004
WO 2004032992 A2 4/2004
WO 2004045696 A1 6/2004
WO 2004050155 A1 6/2004
WO 2004052440 A1 6/2004
WO 2004056290 A1 7/2004
WO 2004056414 A1 7/2004
WO 2004056909 A1 7/2004
WO 2004075944 A2 9/2004
WO 2004089454 A1 10/2004
WO 2005004964 A1 1/2005
WO 2005014055 A2 2/2005
WO 2005061035 A1 7/2005
WO 2005092418 A1 10/2005
WO 2006005349 A2 1/2006
WO 2006009509 A1 1/2006
WO 2006009596 A1 1/2006
WO 2006017439 A2 2/2006
WO 2006021590 A1 3/2006
WO 2006027349 A1 3/2006
WO 2006033234 A1 3/2006
WO 2006037321 A1 4/2006
WO 2006097109 A2 9/2006
WO 2006110695 A2 10/2006
WO 2006112782 A1 10/2006
WO 2006130776 A2 12/2006
WO 2007001526 A2 1/2007
WO 2007038988 A1 4/2007
WO 2007083033 A2 7/2007
WO 2008089770 A1 7/2008
WO 2008104573 A2 9/2008
WO 2008104603 A1 9/2008
WO 2008138351 A1 11/2008
WO 2008138352 A1 11/2008
WO 2008151074 A1 12/2008
WO 2009000277 A1 12/2008
WO 2009012336 A1 1/2009
WO 2009017541 A1 2/2009
WO 2007050685 A3 4/2009
WO 2009043872 A1 4/2009
WO 2009068043 A2 6/2009
WO 2009080265 A1 7/2009
WO 2009108243 A1 9/2009
WO 2010006620 A1 1/2010
WO 2010041084 A1 4/2010
WO 2010054659 A1 5/2010
WO 2010054666 A1 5/2010
WO 2010129362 A1 11/2010
WO 2010130261 A1 11/2010
WO 2010149174 A1 12/2010
WO 2010149175 A1 12/2010
WO 2010151682 A2 12/2010
WO 2011011023 A1 1/2011
WO 2011014201 A1 2/2011
WO 2011019359 A1 2/2011
WO 2011026929 A1 3/2011
WO 2011026930 A1 3/2011
WO 2011063816 A1 6/2011
WO 2011073403 A1 6/2011
WO 2011076211 A1 6/2011
WO 2011079129 A1 6/2011
WO 2011109393 A1 9/2011
WO 2012016570 A2 2/2012
WO 2012016571 A2 2/2012
WO 2012079590 A1 6/2012
WO 2012085124 A1 6/2012
WO 2012126474 A1 9/2012
WO 2012134804 A1 10/2012
WO 2012139214 A1 10/2012
WO 2013010745 A1 1/2013
WO 2013029621 A1 3/2013
WO 2013075725 A1 5/2013
WO 2014062225 A1 4/2014
WO 2014081859 A1 5/2014
WO 2014142917 A1 9/2014
WO 2014142923 A1 9/2014
WO 2014165046 A1 10/2014
WO 15069843 A2 5/2015
WO 2015075841 A1 5/2015
WO 15090338 A1 6/2015
WO 2015089189 A2 6/2015
WO 2015105942 A1 7/2015
WO 15142506 A1 9/2015
WO 2015184365 A1 12/2015
WO 201603323 A1 1/2016
WO 2016008493 A1 1/2016
WO 2016116915 A1 7/2016
WO 2016206701 A1 12/2016
WO 2017185052 A1 10/2017
WO 2018029279 A1 2/2018
WO 2018059637 A1 4/2018
WO 2018134748 A1 7/2018
WO 2018150975 A1 8/2018
WO 2018156589 A2 8/2018
WO 2018219433 A1 12/2018
WO 2019002066 A2 1/2019
WO 2019014344 A1 1/2019
WO 2019070984 A1 4/2019
WO 2019083104 A1 5/2019
WO 2019083839 A1 5/2019
WO 2019099845 A1 5/2019
WO 2019099975 A2 5/2019
WO 2019113203 A1 6/2019
WO 2019123004 A1 6/2019
WO 2019123005 A1 6/2019
WO 2019245679 A1 12/2019
WO 2020006527 A1 1/2020
WO 2020015804 A1 1/2020
WO 2020106822 A1 5/2020
WO 2020125908 A1 6/2020
WO 2020223146 A1 11/2020
WO 2020237286 A1 12/2020
WO 2020251961 A1 12/2020
WO 2020252003 A1 12/2020
WO 2020263859 A1 12/2020
WO 2021034487 A1 2/2021
WO 2021041703 A1 3/2021
WO 2021051158 A1 3/2021
WO 2021077103 A1 4/2021
WO 2021087099 A1 5/2021
WO 2021092271 A1 5/2021
WO 2021097519 A1 5/2021
WO 2021108115 A1 6/2021
WO 2021115840 A1 6/2021
WO 2021127040 A1 6/2021
WO 2021183718 A1 9/2021
WO 2022031520 A1 2/2022
WO 2022031550 A1 2/2022
WO 2022056263 A2 3/2022
WO 2022223978 A1 10/2022
WO 2022223980 A1 10/2022
WO 2022223983 A1 10/2022
WO 2022223985 A1 10/2022
WO 2022223987 A1 10/2022
WO 2022260831 A1 12/2022
WO 2023003682 A1 1/2023
WO 2023055832 A1 4/2023
WO 2023180707 A1 9/2023
WO 2023211421 A1 11/2023
WO 2024112323 A1 5/2024
WO 2024112324 A1 5/2024
WO 2024112325 A1 5/2024
WO 2024112799 A1 5/2024

(56) References Cited

FOREIGN PATENT DOCUMENTS

| | | | |
|---|---|---|---|
| WO | 2024112805 | A1 | 5/2024 |
| WO | 2025193963 | A1 | 9/2025 |
| WO | 2025221562 | A1 | 10/2025 |

OTHER PUBLICATIONS

"Tripartite Biocompatibility Guidance for Medical Devices," DSMA (Apr. 24, 1987).
Akzo Nobel, "Ethomeen C/25 technical data sheet" Mar. 10, 2009.
Amirkhai IL et al., "Nitric Oxide Complexes of Trimethylaluminium" Joumal of Organometallic Chemistry, 149 (1978).
Angus "Chemie GmbHTechnical Data Sheet", AMP-95, TDS 10A (2000).
AU 2014248744 filed Jul. 9, 2015 Examiner's Report dated Jul. 26, 2017.
AU 2015306630 filed Feb. 2, 2017 Office Action dated Aug. 2, 2018.
BR PI 0506836-3 filed Jan. 18, 2005, Technical Report dated Jul. 28, 2015.
BR1120170040301 filed Feb. 21, 2017 Office Action dated Aug. 20, 2019.
CA 2,769,026 filed Jan. 24, 2012 First Examination Report dated Nov. 4, 2013.
CN 201080058895.4 filed Jun. 21, 2012 First Office Action dated Feb. 27, 2014.
CN 201080058895.4 filed Jun. 21, 2012 Second Office Action dated Nov. 3, 2014.
CN 201080058895.4 filed Jun. 21, 2012 Third Office Action dated May 4, 2015.
CN 201480013064.3 filed Sep. 8, 2015 Office Action dated Jun. 29, 2017.
CN 201480013064.3 filed Sep. 8, 2015 Office Action dated Oct. 10, 2016.
CN 20158004662.3 filed Feb. 24, 2017 Office Action dated Jul. 8, 2019.
CN 20158004662.3 filed Feb. 24, 2017 Office Action dated Sep. 20, 2019.
EP 09848341.5 filed Feb. 27, 2012 extended European Search Report dated Apr. 4, 2013.
EP 09848341.5 filed Feb. 27, 2012 supplemental European Search Report dated Nov. 8, 2013.
EP 10840071.4 filed Jul. 4, 2012 Exam Report dated Apr. 29, 2014.
EP 10840071.4 filed Jul. 4, 2012 extended European Search Report dated Apr. 17, 2013.
EP 10840071.4 filed Jul. 4, 2012 Notice of Opposition dated Apr. 24, 2017.
EP 10840071.4 filed Jul. 4, 2012 Office Action dated Jul. 9, 2015.
EP 11751198.0 filed Sep. 28, 2012 Exam Report dated Feb. 7, 2014.
EP 11751198.0 filed Sep. 28, 2012 extended European search report dated Jul. 9, 2013.
EP 14779919.1 filed Sep. 10, 2015 Extended European Search Report dated Aug. 23, 2016.
EP 14779919.1 filed Sep. 10, 2015 Office Action dated Jul. 4, 2017.
EP 15836062.8 filed Feb. 17, 2017 Extended European Search Report dated Feb. 20, 2018.
EP 15836062.8 filed Feb. 17, 2017 Office Action dated Feb. 19, 2019.
EP 16171279.9 filed May 25, 2016 Extended European Search Report, dated Aug. 23, 2016.
EP 16171279.9 filed May 25, 2016 Intent to Grant, dated Jun. 13, 2017.
EP 17201044.9 filed Nov. 10, 2017 Extended European Search Report dated Jan. 18, 2018.
EP 17201044.9 filed Nov. 10, 2017 Office Action dated Jul. 4, 2019.
Hollister, "Vapro intermittent catheter brochure" (2009).
Johnson et al. "Activities of a Nitrofurazone-Containing Urinary Catheter and a Silver Hydrogel Catheter against Multidrug-Resistant Bacteria Characteristic of Catheter-Associated Urinary Tract Infection" Antimicrobial Agents and Chemotherapy, Dec. 1999.
JP 2012-546157 filed Jun. 12, 2012 Decision of Rejection dated Aug. 21, 2015.
JP 2012-546157 filed Jun. 12, 2012 First Office Action dated Sep. 16, 2014.
JP 2015-243156 filed Dec. 14, 2015 Office Action dated Sep. 16, 2016.
JP 2016-501444 filed Sep. 11, 2015 Office Action dated Dec. 14, 2017.
JP 2017-511223 filed Feb. 24, 2017 Office Action dated Jun. 4, 2019.
Lubrizol, "Neutralizing Carbopol®* and Pemulen™* Polymers in Aqueous and Hydroalcoholic Systems" Technical Data Sheet TDS-237 Edition: Sep. 16, 2009.
Moore et al., "The Swelling of Cotton in Water: A Microscopical Study," Textile Research Journal, vol. 20, Issue 9 pp. 620-630, Sep. 1, 1950.
MX/a/2015/009904 filed Jul. 30, 2015 Office Action dated Jun. 29, 2018.
MX/a/2017/002457 filed Feb. 23, 2017 Office Action dated Sep. 4, 2019.
Newman "Intermittent Catheterization and Current Best Practices: Catheter Design and Types"; http://www.medscape.com/viewarticle/745908_8, last accessed May 31, 2013.
Newman et al. "Review of Intermittent Catheterization and Current Best Practices," Urological Nursing, vol. 31, No. 1 pp. 12-29, 48, Jan. 2011.
Norton, J.A. et al., Surgery: Basic Science and Clinical Evidence Springer, 2nd ed., 2008, p. 281.
PCT/US2006/041633 filed Oct. 25, 2006 International Preliminary Report on Patentability dated Mar. 24, 2009.
PCT/US2006/041633 filed Oct. 25, 2006 Search Report dated Aug. 12, 2008.
PCT/US2006/041633 filed Oct. 25, 2006 Written Opinion dated Aug. 12, 2008.
EP 24164460.8 filed Mar. 19, 2024 Extended European Search Report dated Jun. 19, 2024.
PCT/US2022/045084 filed Sep. 28, 2022 International Search Report and Written Opinion dated Jan. 3, 2023.
PCT/US2022/026177 filed Apr. 25, 2022 International Search Report & Written Opinion dated Mar. 20, 2023.
U.S. Appl. No. 17/796,611, filed Jul. 29, 2022 Non-Final Office Action dated Mar. 20, 2025.
PCT/US2009/055389 filed Aug. 28, 2009 International Search Report dated Oct. 20, 2009.
PCT/US2009/055389 filed Aug. 28, 2009 Written Opinion dated Oct. 20, 2009.
PCT/US2009/055395 filed Aug. 28, 2009 International Preliminary Report on Patentability dated Jan. 31, 2012.
PCT/US2009/055395 filed Aug. 28, 2009 International Search Report dated Oct. 15, 2009.
PCT/US2009/055395 filed Aug. 28, 2009 Written Opinion dated Oct. 15, 2009.
PCT/US2010/061597 filed Dec. 21, 2010 International Preliminary Report on Patentability dated Jun. 26, 2012 and Written Opinion dated Feb. 28, 2011.
PCT/US2010/061597 filed Dec. 21, 2010 International Search Report dated Feb. 28, 2011.
PCT/US2011/026681 filed Mar. 1, 2011 International Preliminary Report on Patentability dated Sep. 4, 2012.
PCT/US2011/026681 filed Mar. 1, 2011 International Search Report dated Apr. 27, 2011.
PCT/US2011/026681 filed Mar. 1, 2011 Written Opinion dated Apr. 27, 2011.
PCT/US2014/024231 filed Mar. 12, 2014 International Search Report and Written Opinion dated Jul. 10, 2014.
PCT/US2021/043771 filed Jul. 29, 2021 International Search Report and Written Opinion dated Jan. 24, 2022.
PCT/US2021/044021 filed Jul. 30, 2021 International Search Report and Written Opinion dated Jan. 24, 2022.

(56) References Cited

OTHER PUBLICATIONS

PCT/US2021/049867 filed Sep. 10, 2021 International Search Report and Written Opinion dated Mar. 11, 2022.
PCT/US2022/029431 filed May 16, 2022 International Search Report and Written Opinion dated Sep. 15, 2022.
PCT/US2022/035565 filed Jun. 29, 2022 International Search Report and Written Opinion dated Sep. 27, 2022.
PCTUS2018054378 filed Oct. 4, 2018 International Preliminary Report on Patentability dated Jan. 2, 2019.
PCTUS2018054378 filed Oct. 4, 2018 International Search Report and Written opinion dated Jan. 2, 2019.
Peppas, "Hydrogels," Biomaterial Science: An Introduction to Materials in Medicine. 2nd Edition, pp. 100-107, Aug. 18, 2004.
Piyush Gupta et al. Hydrogels: from controlled release to pH-responsive drug delivery, May 2002, DDT vol. 7, No. 10, pp. 569-579. (Year: 2002).
RU 2015140616 filed Sep. 24, 2015 Office Action dated Feb. 21, 2018.
U.S. Appl. No. 12/091,916, filed Feb. 2, 2009 Final Office Action dated Sep. 22, 2011.
U.S. Appl. No. 12/091,916, filed Feb. 2, 2009 Non-Final Office Action dated May 10, 2011.
U.S. Appl. No. 12/091,916, filed Feb. 2, 2009 Non-Final Office Action dated Nov. 24, 2010.
U.S. Appl. No. 12/091,916, filed Feb. 2, 2009 Notice of Allowance dated Aug. 17, 2012.
U.S. Appl. No. 13/387,447, filed Mar. 22, 2012 Advisory Action dated Feb. 27, 2014.
U.S. Appl. No. 13/387,447, filed Mar. 22, 2012 Examiner's Answer dated Oct. 5, 2016.
U.S. Appl. No. 13/387,447, filed Mar. 22, 2012 Final Office Action dated Dec. 11, 2013.
U.S. Appl. No. 13/387,447, filed Mar. 22, 2012 Final Office Action dated Oct. 31, 2014.
U.S. Appl. No. 13/387,447, filed Mar. 22, 2012 Final Office Action dated Oct. 5, 2015.
U.S. Appl. No. 13/387,447, filed Mar. 22, 2012 Non-Final Office Action dated Jan. 15, 2013.
U.S. Appl. No. 13/387,447, filed Mar. 22, 2012 Non-Final Office Action dated Jul. 15, 2014.
U.S. Appl. No. 13/387,447, filed Mar. 22, 2012 Non-Final Office Action dated Jun. 6, 2013.
U.S. Appl. No. 13/387,447, filed Mar. 22, 2012 Non-Final Office Action dated Mar. 12, 2015.
U.S. Appl. No. 13/387,447, filed Mar. 22, 2012 Notice of Allowance dated Jul. 30, 2018.
U.S. Appl. No. 13/387,447, filed Mar. 22, 2012 Patent Board Decision dated Jun. 1, 2018.
U.S. Appl. No. 13/389,753, filed Mar. 20, 2012 Decision on Appeal dated Jun. 29, 2017.
U.S. Appl. No. 13/389,753, filed Mar. 20, 2012 Examiner's Answer dated Aug. 27, 2015.
U.S. Appl. No. 13/389,753, filed Mar. 20, 2012 Final Office Action dated Dec. 10, 2014.
U.S. Appl. No. 13/389,753, filed Mar. 20, 2012 Non-Final Office Action dated Jul. 21, 2014.
U.S. Appl. No. 13/389,753, filed Mar. 20, 2012 Notice of Allowance dated Jul. 5, 2017.
U.S. Appl. No. 13/516,660, filed Aug. 27, 2012 Advisory Action dated Nov. 19, 2019.
U.S. Appl. No. 13/516,660, filed Aug. 27, 2012 Advisory Action dated Sep. 22, 2016.
U.S. Appl. No. 13/516,660, filed Aug. 27, 2012 Board Decision dated Jan. 22, 2019.
U.S. Appl. No. 13/516,660, filed Aug. 27, 2012 Examiner's Answer dated Nov. 22, 2017.
U.S. Appl. No. 13/516,660, filed Aug. 27, 2012 Final Office Action dated Jun. 29, 2016.
U.S. Appl. No. 13/516,660, filed Aug. 27, 2012 Final Office Action dated Sep. 9, 2019.
U.S. Appl. No. 13/516,660, filed Aug. 27, 2012 Non-Final Office Action dated Jan. 8, 2020.
U.S. Appl. No. 13/516,660, filed Aug. 27, 2012 Non-Final Office Action dated Mar. 15, 2019.
U.S. Appl. No. 13/516,660, filed Aug. 27, 2012 Non-Final Office Action dated Mar. 8, 2016.
U.S. Appl. No. 13/516,660, filed Aug. 27, 2012 Notice of Allowance dated Oct. 27, 2020.
U.S. Appl. No. 13/582,698, filed Sep. 4, 2012 Non-Final Office Action dated Sep. 24, 2014.
U.S. Appl. No. 13/662,278, filed Oct. 26, 2012 Board Decision dated Aug. 23, 2018.
U.S. Appl. No. 13/662,278, filed Oct. 26, 2012 Examiner's Answer dated Jun. 2, 2017.
U.S. Appl. No. 13/662,278, filed Oct. 26, 2012 Final Office Action dated Feb. 20, 2015.
U.S. Appl. No. 13/662,278, filed Oct. 26, 2012 Final Office Action dated Oct. 19, 2016.
U.S. Appl. No. 13/662,278, filed Oct. 26, 2012 Non-Final Office Action dated Jul. 7, 2016.
U.S. Appl. No. 13/662,278, filed Oct. 26, 2012 Non-Final Office Action dated Sep. 12, 2014.
U.S. Appl. No. 13/662,278, filed Oct. 26, 2012 Non-Final Office Action dated Sep. 17, 2015.
U.S. Appl. No. 13/802,095, filed Mar. 13, 2013 Non-Final Office Action dated Aug. 15, 2014.
U.S. Appl. No. 13/802,095, filed Mar. 13, 2013 Notice of Allowance dated Nov. 28, 2014.
U.S. Appl. No. 14/681,023, filed Apr. 7, 2015 Non-Final Office Action dated Nov. 9, 2016.
U.S. Appl. No. 14/681,023, filed Apr. 7, 2015 Notice of Allowance dated Mar. 8, 2017.
U.S. Appl. No. 14/707,954, filed May 8, 2015 Non-Final Office Action dated Dec. 1, 2016.
U.S. Appl. No. 15/506,723, filed Feb. 24, 2017 Final Office Action dated Dec. 9, 2019.
U.S. Appl. No. 15/506,723, filed Feb. 24, 2017 Non-Final Office Action dated Aug. 27, 2019.
U.S. Appl. No. 15/506,723, filed Feb. 24, 2017 Notice of Allowance dated Jul. 29, 2020.
U.S. Appl. No. 15/639,844, filed Jun. 30, 2017 Non-Final Office Action dated Jul. 10, 2019.
U.S. Appl. No. 15/639,844, filed Jun. 30, 2017 Notice of Allowance dated Aug. 13, 2019.
U.S. Appl. No. 15/669,697, filed Aug. 4, 2017 Non-Final Office Action dated Oct. 18, 2018.
U.S. Appl. No. 15/669,697, filed Aug. 4, 2017 Notice of Allowance dated Mar. 1, 2019.
U.S. Appl. No. 15/724,879, filed Oct. 4, 2017 Advisory Action dated Jan. 29, 2019.
U.S. Appl. No. 15/724,879, filed Oct. 4, 2017 Examiner's Answer dated Jul. 25, 2019.
U.S. Appl. No. 15/724,879, filed Oct. 4, 2017 Final Office Action dated Dec. 4, 2018.
U.S. Appl. No. 15/724,879, filed Oct. 4, 2017 Non-Final Office Action dated Jul. 19, 2018.
U.S. Appl. No. 15/724,879, filed Oct. 4, 2017 Notice of Allowance dated Aug. 14, 2020.
U.S. Appl. No. 15/724,879, filed Oct. 4, 2017 PTAB Decision on Appeal dated Jul. 1, 2020.
U.S. Appl. No. 15/724,879, filed Oct. 4, 2017 Restriction Requirement dated Mar. 7, 2018.
U.S. Appl. No. 16/453,809, filed Jun. 26, 2019 Notice of Allowance dated Apr. 14, 2020.
U.S. Appl. No. 17/114,275, filed Dec. 7, 2020 Final Office Action dated May 23, 2023.
U.S. Appl. No. 17/114,275, filed Dec. 7, 2020 Non-Final Office Action dated Jan. 31, 2023.
U.S. Appl. No. 17/114,275, filed Dec. 7, 2020 Notice of Allowance dated Aug. 9, 2023.
Wong, "Hydrogels, water-absorbing polymers" Catalyst, vol. 18, Issue 1, pp. 18-21, Sep. 2007.

(56) References Cited

OTHER PUBLICATIONS

PCT/US2022/050645 filed Nov. 21, 2022 International Search Report and Written Opinion dated Jun. 28, 2023.
PCT/US2022/050646 filed Nov. 21, 2022 International Search Report and Written Opinion dated May 30, 2023.
PCT/US2022/050648 filed Nov. 21, 2022 International Search Report and Written Opinion dated Jun. 16, 2023.
PCT/US2023/080761 filed Nov. 21, 2023 International Search Report and Written Opinion dated Apr. 9, 2024.
PCT/US2023/080769 filed Nov. 21, 2023 International Search Report and Written Opinion dated Mar. 15, 2024.
PCT/US2025/019799 filed Mar. 13, 2025 International Search Report and Written Opinion dated Jun. 4, 2025.
PCT/US2025/023972 filed Apr. 9, 2025 International Search Report and Written Opinion dated Sep. 18, 2025.
U.S. Appl. No. 17/796,611, filed Jul. 29, 2022 Final Office Action dated Sep. 24, 2025.
U.S. Appl. No. 18/019,464, filed Feb. 2, 2023 Non-Final Office Action dated Jul. 30, 2025.
U.S. Appl. No. 18/019,464, filed Feb. 2, 2023 Restriction Requirement dated May 6, 2025.
U.S. Appl. No. 18/019,647, filed Feb. 3, 2023 Non-Final Office Action dated Jul. 31, 2025.
U.S. Appl. No. 18/019,647, filed Feb. 3, 2023 Restriction Requirement dated May 8, 2025.
U.S. Appl. No. 18/025,875, filed Mar. 10, 2023 Non-Final Office Action dated Aug. 28, 2025.
U.S. Appl. No. 18/025,875, filed Mar. 10, 2023 Restriction Requirement dated Jun. 4, 2025.
U.S. Appl. No. 17/796,611, filed Jul. 29, 2022 Advisory Action dated Nov. 28, 2025.
U.S. Appl. No. 17/796,611, filed Jul. 29, 2022 Non-Final Office Action dated Jan. 8, 2026.
U.S. Appl. No. 18/019,464, filed Feb. 2, 2023 Notice of Allowance dated Nov. 25, 2025.
U.S. Appl. No. 18/019,647, filed Feb. 3, 2023 Non-Final Office Action dated Nov. 17, 2025.
U.S. Appl. No. 18/025,875, filed Mar. 10, 2023 Notice of Allowance dated Jan. 14, 2026.
U.S. Appl. No. 18/536,063, filed Dec. 11, 2023 Non-Final Office Action dated Nov. 12, 2025.
U.S. Appl. No. 18/580,449, filed Jan. 19, 2024 Non-Final Office Action dated Feb. 2, 2026.
U.S. Appl. No. 18/641,181, filed Apr. 19, 2024 Non-Final Office Action dated Jan. 12, 2026.
U.S. Appl. No. 18/019,647, filed Feb. 3, 2023 Notice of Allowance dated Mar. 27, 2026.
U.S. Appl. No. 18/536,063, filed Dec. 11, 2023 Notice of Allowance dated Mar. 31, 2026.
U.S. Appl. No. 18/568,208, filed Dec. 7, 2023 Non-Final Office Action dated Apr. 1, 2026.
U.S. Appl. No. 18/641,181 filed Apr. 19, 2024 Final Office Action dated Apr. 28, 2026.

* cited by examiner

LABELING AND PACKAGING SYSTEM AND METHODS

BACKGROUND

Labeling and packaging systems are commonly used in various industries to provide information and protection for products. In the field of medical devices, it is important to have efficient and secure packaging systems that ensure the integrity and safety of the devices during storage, transportation, and use. Previous approaches to labeling and packaging systems have focused on different aspects such as ease of opening, tamper-evident features, and integration with the primary packaging.

Previous approaches include applying labels directly onto the primary packaging, often using adhesives or similar means. These labels typically include printed information about the product, such as its name, instructions for use, and any relevant warnings or regulatory information. While these labels are widely used, they can sometimes be difficult to remove without damaging the primary packaging. Additionally, these labels can inhibit access to the contents of the packaging.

Other approaches include incorporating tear lines or perforations into the primary packaging itself. These tear lines are designed to facilitate opening of the packaging by providing a predetermined path along which the packaging can be torn. However, these tear lines may not always be user-friendly or intuitive, and there is a risk of accidental tearing or damage to the packaging during transport, storage, or the opening process causing the contents to spill onto the floor or a nonsterile surface, compromising the sterility of the medical device.

Disclosed herein are labeling and packaging systems and associated methods thereof directed to address the foregoing.

SUMMARY

In some aspects, the techniques described herein relate to a labeling and packaging system including, a primary packaging having a top seam and a bottom seam and defining an interior cavity, a medical device disposed within the interior cavity, and a label system including, a first body extending over a frontal plane and defining a front surface and a rear surface and having a length (L) and a width (W), the rear surface coupled to a front surface of the primary packaging, a first right handle coupled to a right side of a top edge of the first body, a first left handle coupled to a left side of the top edge of the first body, and a tear line extending longitudinally from the top edge of the first body, between the first right handle and the first left handle, the tear line having a distance (d) that is less than the length (L) of the first body, the tear line configured to facilitate separation there along when the first right handle is urged in an opposite direction from the first left handle.

In some aspects, the techniques described herein relate to a system, wherein the distance (d) is between 20% and 80% of the length (L) of the first body.

In some aspects, the techniques described herein relate to a system, wherein the length (L) of the first body is equal to or less than a second length (L2) of the primary packaging.

In some aspects, the techniques described herein relate to a system, further including a tear stop disposed at a bottom end of the tear line In some aspects, the techniques described herein relate to a system, wherein the tear stop includes a reinforcement displaying an increased tensile strength to prevent further separation of the first body.

In some aspects, the techniques described herein relate to a system, wherein the tear stop includes a frangible line angled relative to the tear line and configured to mitigate further separation along that tear line at a predetermined position on the primary packaging.

In some aspects, the techniques described herein relate to a system, further including a cut extending from the top edge of the first body and disposed between the first right handle and the first left handle, the cut extending through one or both of a portion of the first body and a portion of the top seam of the primary packaging.

In some aspects, the techniques described herein relate to a system, wherein the rear surface is coupled to the front surface of the primary packaging by one or more of adhesive sealing, mechanical sealing, energized sealing, heat sealing, and ultrasonic welding.

In some aspects, the techniques described herein relate to a system, further including a second right handle extending from a top edge of the first right handle and including a first fold line disposed therebetween, and a second left handle extending from a top edge of the first left handle and including a second fold line disposed therebetween, and a second body, coupled to both the second right handle and the second left handle along a first edge of the second body.

In some aspects, the techniques described herein relate to a system, wherein an outer perimeter of the second right handle aligns with an outer perimeter of the first right handle when folded along the first fold line, and an outer perimeter of the second left handle aligns with an outer perimeter of the first left handle when folded along the second fold line, and a surface of the second body is configured to couple with a rear side of the primary packaging.

In some aspects, the techniques described herein relate to a system, wherein the second body includes a second tear line extending from the first edge of the second body along a second distance (d2).

In some aspects, the techniques described herein relate to a method of opening a packaging and label system including, providing a primary packaging having a top seam and a bottom seam and defining an interior cavity, a medical device disposed within the interior cavity, and a label system having a body, a rear surface of the body coupled with a front surface of the primary packaging, grasping a first right handle and a first left handle of the label system, the first right handle coupled to a right side of a top edge of the body, and the first left handle coupled to a left side of the top edge of the body, urging the first right handle in an opposite direction from the first left handle along an axis extending at an angle relative to a longitudinal axis of the primary packaging, separating the body along a tear line extending longitudinally, and tearing a portion of the primary packaging to access the medical device.

In some aspects, the techniques described herein relate to a method, wherein in the tear line is a line of weakness extending along the body by a distance (d) to facilitate separation therealong, the distance (d) being less than a longitudinal length (L) of the body.

In some aspects, the techniques described herein relate to a method, wherein the distance (d) of the tear line is less than a longitudinal length (L2) of the primary packaging.

In some aspects, the techniques described herein relate to a method, further including a tear stop disposed at a bottom end of the tear line and configured to prevent further separation of the body beyond the distance (d).

In some aspects, the techniques described herein relate to a system, wherein the tear stop includes one of a reinforcement or a frangible line angled relative to the tear line and configured to mitigate further separation along that tear line at a predetermined position on the primary packaging.

In some aspects, the techniques described herein relate to a method, wherein coupling the rear surface of the body to the front surface of the primary packaging includes one or more of adhesive sealing, mechanical sealing, energized sealing, heat sealing, and ultrasonic welding.

In some aspects, the techniques described herein relate to a method of manufacturing a label and packaging system including, forming a primary packaging having a top seam and a bottom seam, a front surface and a rear surface, the primary packaging defining an interior cavity containing a medical device, and coupling a rear surface of a body of a labeling system to the front surface of the primary packaging, the labeling system including a first right handle extending from a right side of a top edge of the body, and a first left handle extending from a left side of the top edge of the body.

In some aspects, the techniques described herein relate to a method, further including folding a second right handle relative to the first right handle along a first fold line such that an outer perimeter of the second right handle aligns with the outer perimeter of the first right handle, and folding a second left handle relative to the first left handle along a second fold line such that an outer perimeter of the second left handle aligns with the outer perimeter of the first left handle.

In some aspects, the techniques described herein relate to a method, further including coupling a surface of a second body to the rear surface of the primary packaging.

In some aspects, the techniques described herein relate to a method, wherein coupling the rear surface of the body to the front surface of the primary packaging includes one or more of adhesive sealing, mechanical sealing, energized sealing, heat sealing, and ultrasonic welding.

In some aspects, the techniques described herein relate to a method, further including forming a cut disposed between the first right handle and the first left handle and extending from the top edge of the body, the cut extending through one or both of the body and a portion of the top seam.

BRIEF DESCRIPTION OF DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein. It is understood that the drawings are diagrammatic and schematic representations of exemplary embodiments of the invention and are neither limiting nor necessarily drawn to scale.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "right," "left," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise. Also, the words "including," "has," and "having," as used herein, including the claims, shall have the same meaning as the word "comprising."

In the following description, the terms "or" and "and/or" as used herein are to be interpreted as inclusive or meaning any one or any combination. As an example, "A, B or C" or "A, B and/or C" mean "any of the following, A, B, C, A and B, A and C, B and C, A, B and C." An exception to this definition will occur only when a combination of elements, components, functions, steps or acts are in some way inherently mutually exclusive.

Figure 1:
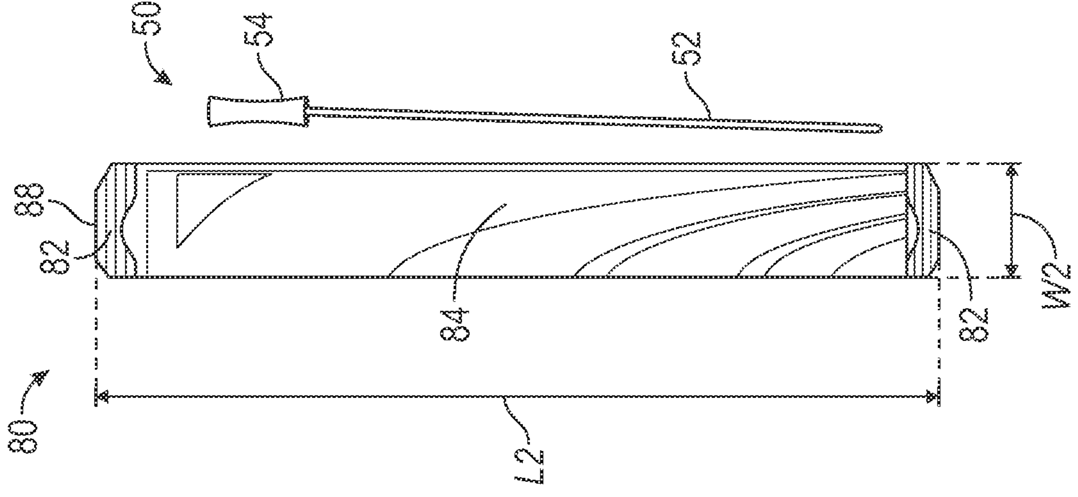
FIG. 1 shows an exploded view of a label and packaging system generally including a label system, a primary packaging, and a medical device, in accordance with embodiments disclosed herein.
Figure 1:
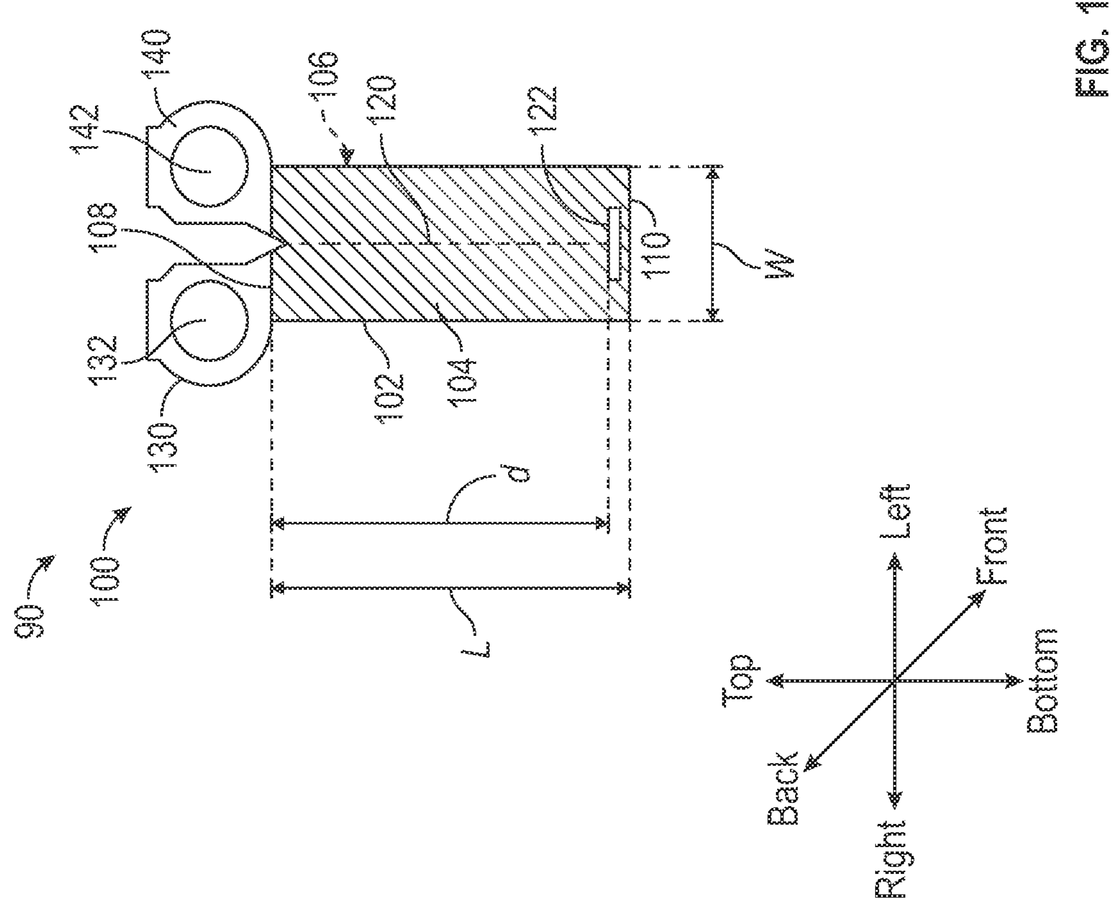

To assist in the description of embodiments described herein, as shown in FIG. 1, a sagittal axis extends between the front and the back. A longitudinal axis extends between the top and the bottom. A frontal axis extends between the right and the left. A frontal plane is defined by the longitudinal axis and the frontal axis. A sagittal plane is defined by the longitudinal axis and the sagittal axis. A transverse plane is defined by the frontal axis and the sagittal axis.

Unless defined otherwise, all technical and scientific terms used herein have the same meaning as commonly understood by those of ordinary skill in the art.

Figure 2A:
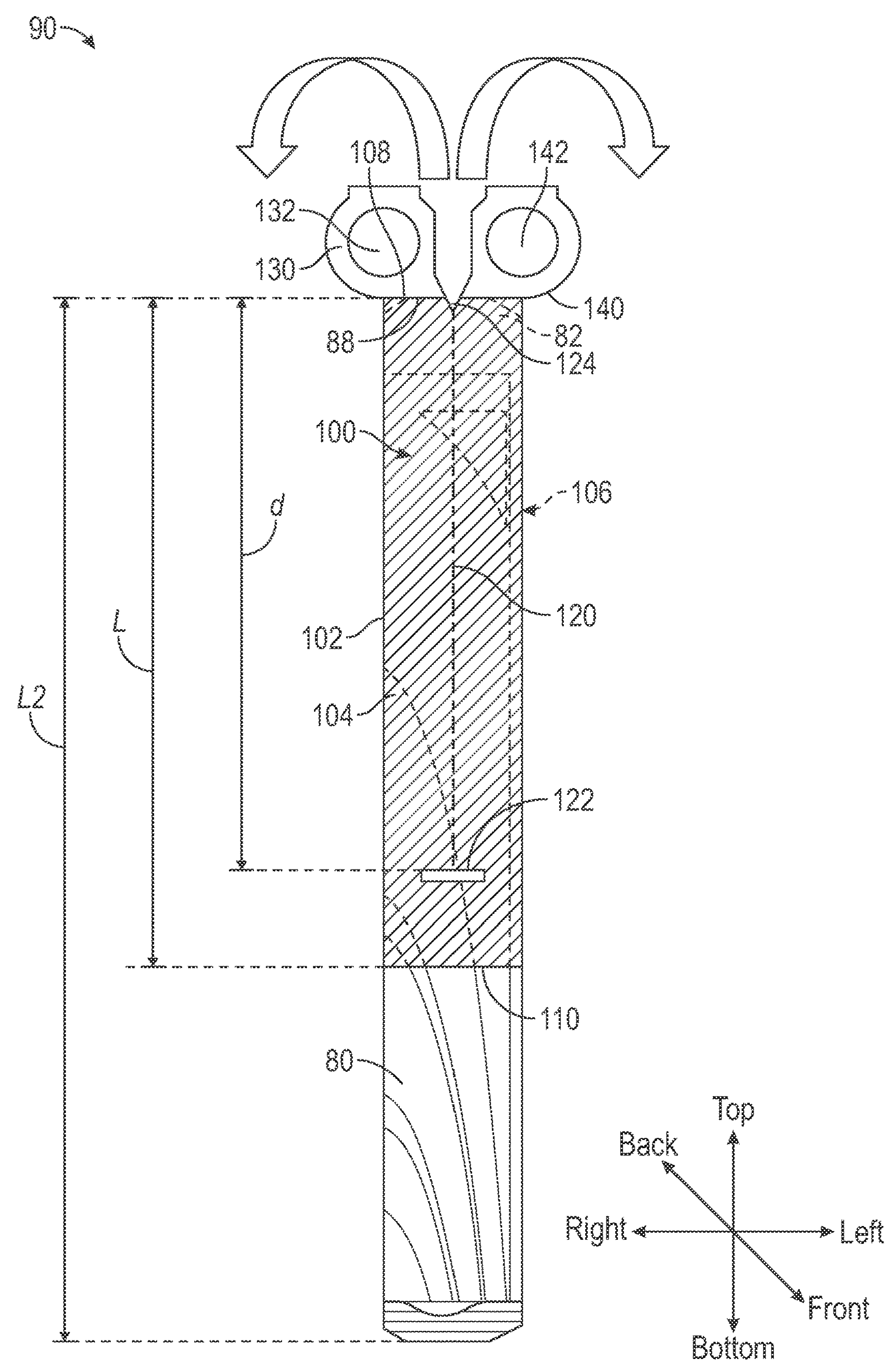
FIGS. 2A-2B show perspective views of the label and packaging system of FIG. 1 in an assembled state, in accordance with embodiments disclosed herein.

FIG. 1 shows an exploded view of a label and packaging system 90 generally including a label system 100, a primary packaging 80 and a medical device 50. Exemplary medical devices can include catheters, intermittent catheters, Foley catheters, balloon catheters, indwelling catheters, peritoneal catheters, pleural drainage catheters, or the like. However, these examples are not intended to be limiting and it will be appreciated that other products or types of medical devices are also contemplated. The primary packaging 80 is configured to contain the medical device 50 therein and the label system 100 is configured to couple with the primary packaging. FIG. 2A shows the label and packaging system 90 in an assembled state.

In an embodiment, the primary packaging 80 is formed of one or more layers of material folded and sealed along one or more seams 82 to define an interior cavity therein. In an embodiment, the interior cavity can define a sterile environment. The one or more layers of material can include the same material or different materials. Exemplary materials of the one or more layers of material include organic or synthetic materials, woven or non-woven materials, plastic, polymers, metal, alloys, composites, foils, paper, wax paper, combinations thereof, or the like.

In an embodiment, the one or more layers of material define a fluid impermeable, liquid impermeable, and/or gaseous impermeable layer. For example, the one or more layers of material define a water impermeable layer and/or an oxygen impermeable layer. As such, the medical device 50 can be maintained in a sterile and/or wetted environment during storage and transport up until the primary package 80 is opened. In an embodiment, the one or more seams 82 can be secured using adhesive sealing, mechanical sealing, energized sealing such as heat sealing, ultrasonic welding, combinations thereof, or the like.

In an embodiment, the medical device 50 includes a sterile portion 52 configured to be disposed within the body of the patient, and a non-sterile portion 54 configured to be handled by the user to facilitate manipulating the medical device 50 without touching the sterile portion 52. For example, where the medical device 50 is an intermittent catheter, the sterile portion 52 can be the catheter tube, configured to be disposed within the urethra or bladder of the patient. The non-sterile portion 54 can be a finger grip or funnel configured to be grasped by the user to facilitate manipulating the medical device 50 without having to touch the catheter tube, sterile portion 52. In an embodiment, the medical device 50 is oriented within the primary packaging 80 with the non-sterile portion 54 positioned adjacent a top edge 88 of the primary packaging. As described in more detail herein, opening the primary packaging 80 can involve tearing a portion of the primary packaging 80. In an embodiment, tearing the primary packaging can begin proximate the top edge 88 to provide access to the non-sterile portion 54 first while maintaining the sterile portion 52 within the primary packaging 80.

In an embodiment, the label system 100 generally includes a body 102 extending over a frontal plane and defining a front surface 104 and a back surface 106. The body 102 defines a length (L) and a width (W). The label system 100 further includes a tear line 120 extending along a longitudinal axis from a top edge 108 towards a bottom edge 110, to a point that is above the bottom edge 110 of the body 102. In an embodiment, the tear line 120 extends along a distance (d) that is less than the length (L) of the body 102. In an embodiment, the tear line 120 extends a distance (d) that is between 20% and 80% of the length (L) of the body 102. However, it will be appreciated that greater or lesser distances are also contemplated.

In an embodiment, as shown in FIG. 2A, the label system 100 can be coupled with the primary packaging 80 with a central longitudinal axis of the body 102 aligning with a central longitudinal axis of the primary packaging 80. In an embodiment, the label system 100 can be coupled with the primary packaging 80 in an offset position, with a central longitudinal axis of the body 102 disposed to either the right side or the left side of the central longitudinal axis of the primary packaging 80. In an embodiment, the left edge of the body 102 can be aligned with the left edge of the primary packaging 80. In an embodiment, the right edge of the body 102 can be aligned with the right edge of the primary packaging 80.

The tear line 120 is a die cut line, laser cut line, perforation, frangible line, score line, groove, or similar line of weakness configured to facilitate separation of the body 102 therealong, as described in more detail herein. In an embodiment, the tear line 120 is separated along an entire length (distance (d)) of the tear line 120. In an embodiment, the tear line 120 is separated along a portion or a plurality of portions along the distance (d) of the tear line 120, e.g. to form a frangible perforation, or the like. In an embodiment, the tear line 120 is intact along the distance (d) of the tear line 120, e.g. to form a score line, groove line, or the like. As shown, the tear line 120 extends linearly, however, other shaped tear lines are also contemplated including curved, wavy, closed curve, or the like. In an embodiment, as shown in FIG. 2A, the tear line 120 extends parallel to the longitudinal axis of the body 102. In an embodiment, the tear line 120 extends at an angle to the longitudinal axis of the body 102.

In an embodiment, as shown in FIG. 2A the label system 100 includes a reinforcement 122 tear stop 122 disposed between a bottom of the tear line 120 and the bottom edge 110 of the body 102. The tear stop 122 is configured to prevent further separation of the body 102 along the tear line 120. In an embodiment, the tear stop 122 is a reinforced portion made of the same material as the body 102. In an embodiment, the tear stop 122 is a reinforced portion made of a different material from the body 102 having an increased tensile strength to mitigate or prevent tearing.

Figure 2B:
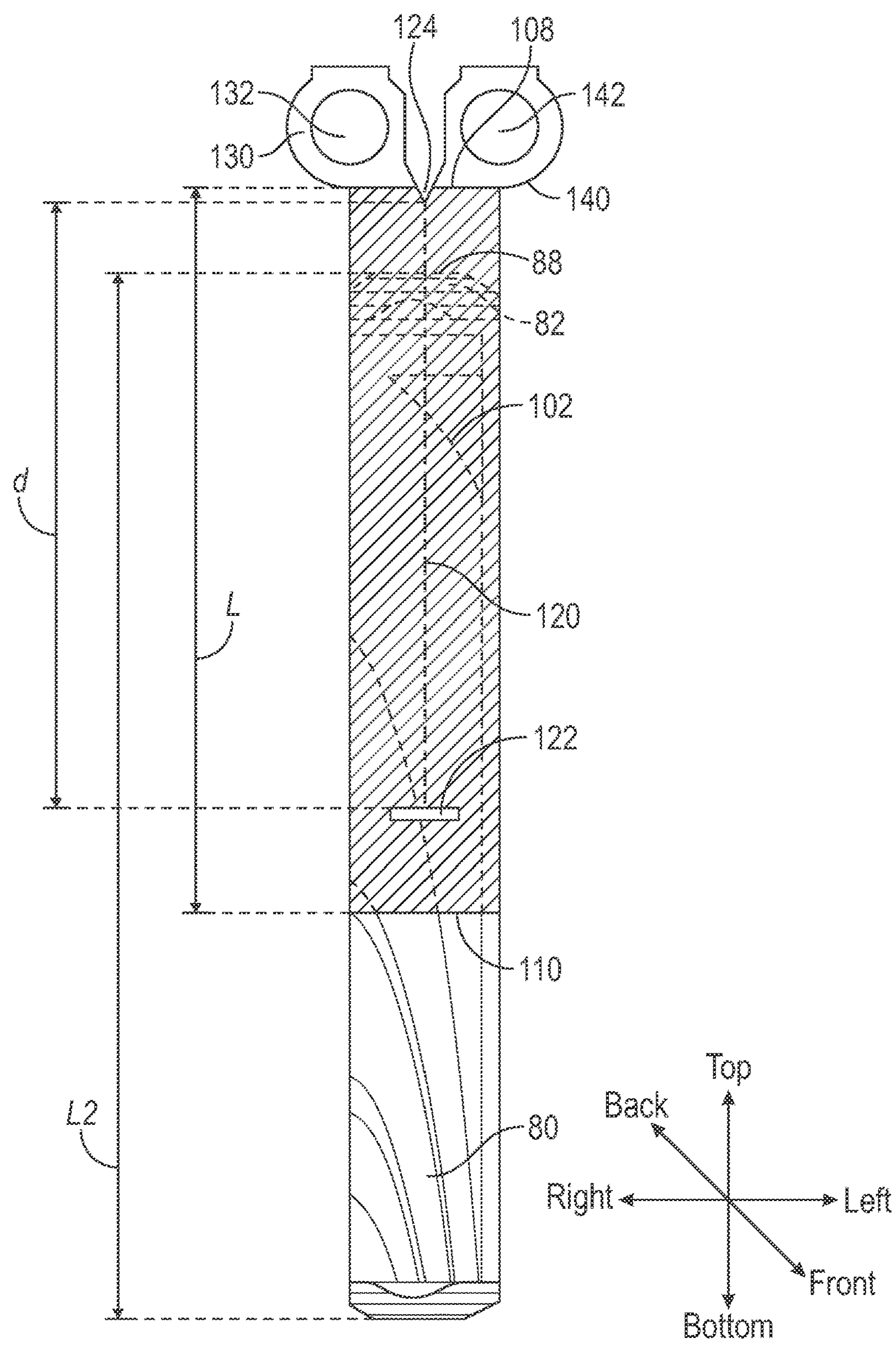
Figure 2C:
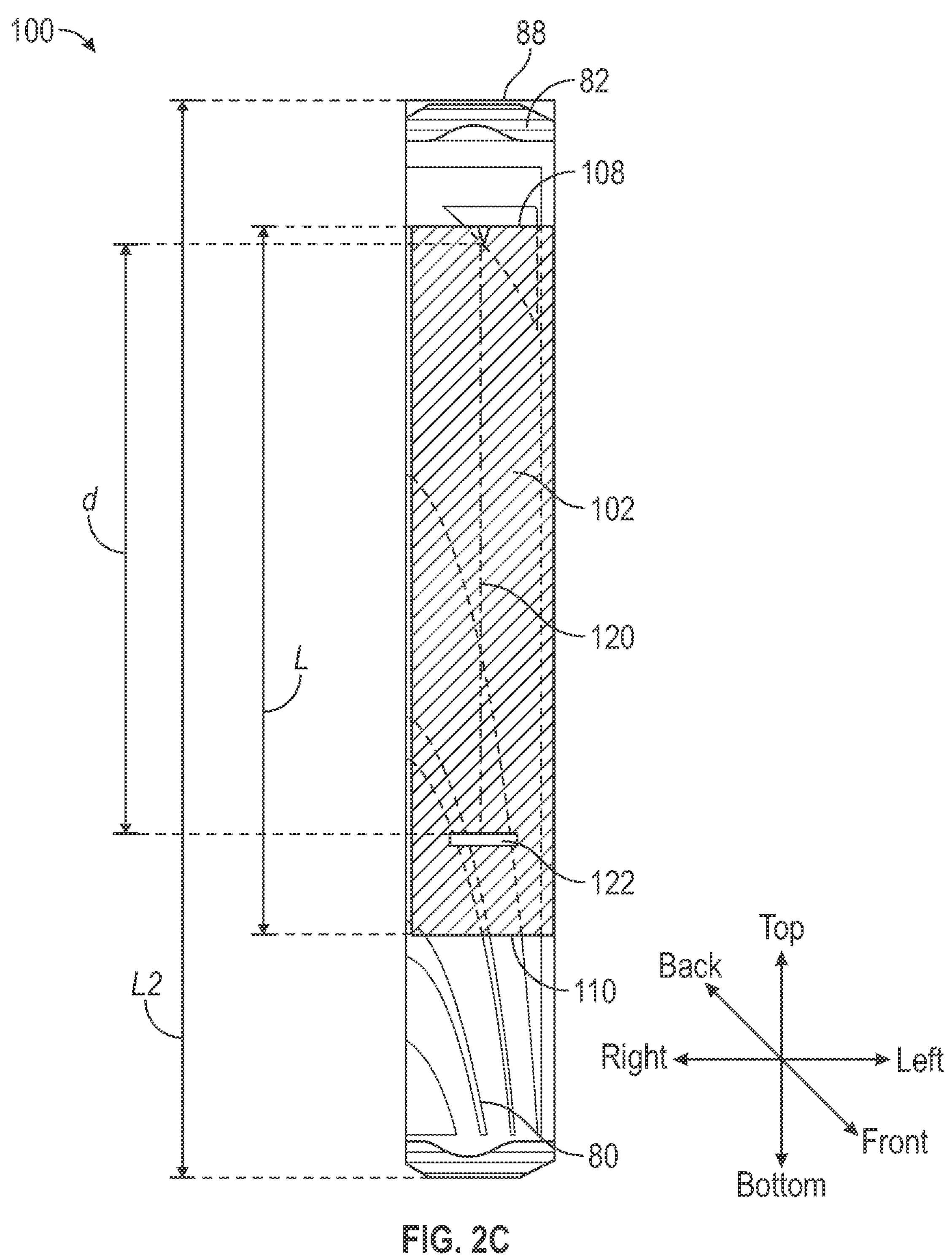
FIG. 2C shows a perspective view of a label system without handles and a packaging system in an assembled state, in accordance with embodiments disclosed herein.
Figure 2D:
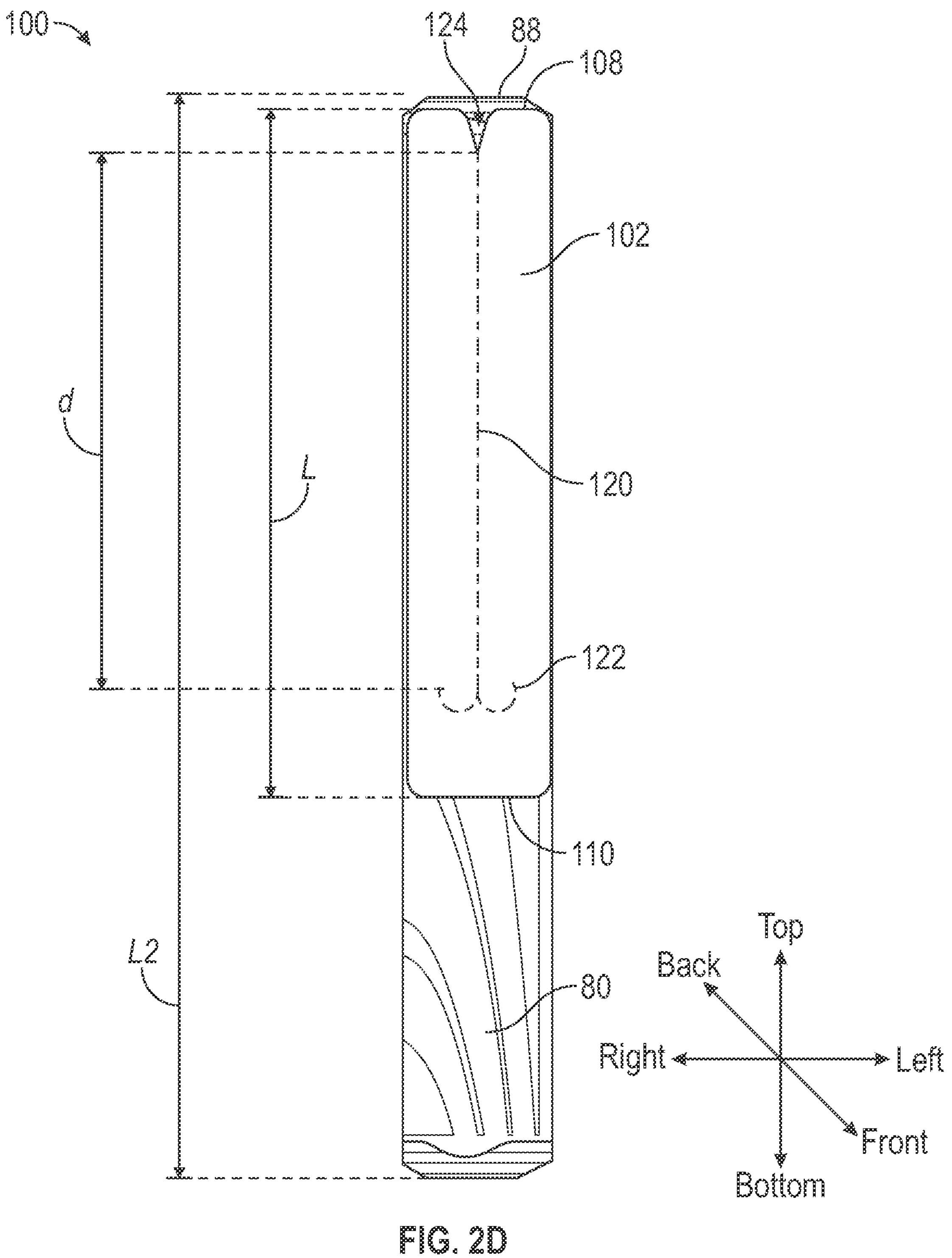
FIG. 2D shows a perspective view of a label system without handles and with a frangible tear stop in an assembled state with a packaging system, in accordance with embodiments disclosed herein.

In an embodiment, as shown in FIG. 2D, the tear stop 122 includes one or more frangible lines such as a die cut line, laser cut line, perforation, frangible line, score line, groove, or similar line of weakness as described herein extending at an angle relative to the axial length of the tear line 120. For example, as shown in FIG. 2D, the tear stop 122 includes a first frangible line extending from the bottom end of the tear line 120 through a first arc, and a second frangible line extending from the bottom end of the tear line 120 through a second arc in an opposite direction from the first arc. One or both of the first arc and the second arc can extend through an arc radius of between 5° degrees and 275°. However it will be appreciated that greater or lesser arc radii are also contemplated. It will also be appreciated that other numbers, angles, shapes, and configurations of frangible lines are also contemplated to be included in the tear stop 122. Advantageously, the frangible line tear stop 122 redirects the direction of the tear, from the axis of the tear line 120 to prevent further separation of the packaging 80 therealong. For example, as shown in FIG. 2D, the semi-circular shape of the tear stop 122 redirects the direction of the tear back on itself to mitigate further tearing momentum along the axis of the tear line 120 and arrest the separation of the primary packaging 80 at a predetermined location thereon.

The label system 100 further includes a right handle 130 and a left handle 140 each extending upwards from the top edge 108 of the body 102. The right handle 130 is coupled with a right side of the top edge 108 of the body 102 and the left handle 140 is coupled with a left side of the top edge 108 of the body 102. In an embodiment one or both of the right handle and the left handle are formed integrally with the body 102 as a single monolithic piece. In an embodiment one or both of the right handle and the left handle are formed separately and coupled with the body 102 using adhesive sealing, mechanical sealing, energized sealing such as heat sealing, ultrasonic welding, combinations thereof, or the like. In an embodiment one or more of the right handle, left handle and the body 102 are formed of the same material. In an embodiment one or more of the right handle, left handle and the body 102 are formed of different materials.

Each of the right handle 130 and the left handle 140 are configured to facilitate grasping the body 102 by a user. For example, as shown in FIG. 1, the right handle 130 defines a right finger loop having an aperture 132 and configured to receive a first digit of a user therethrough. Similarly the left handle 140 defines a left finger loop having an aperture 142 and configured to receive a second digit of a user therethrough. It will be appreciated, however, the finger loop handles of the right handle 130 and the left handle 140 are not intended to be limiting and that other shaped handles for the right handle 130 and the left handle 140 are also contemplated. Exemplary handles include a handle having two or more apertures each configured to receive at least a digit of the user, a finger loop configured to receive two or more digits, straight handles, curved handles, T-shaped handles, combinations thereof, or the like.

As shown in FIGS. 2A-2C, in an embodiment, the body 102 can be coupled to the primary packaging 80. For example, the back surface 106 of the body 102 can be coupled with a front surface 84 of the primary packaging 80 using adhesive sealing, mechanical sealing, energized sealing such as heat sealing, ultrasonic welding, combinations thereof, or the like. In an embodiment, as shown in FIG. 2A, the top edge 108 of the body 102 can be aligned with the top edge 88 of the primary packaging 80. In an embodiment, as shown in FIG. 2B, the top edge 108 of the body 102 can be positioned above the top edge 88 of the primary packaging 80, i.e., the body 102 can be positioned such that the top edge 108 extends beyond the top edge 88 of the primary packaging 80. In an embodiment, as shown in FIG. 2C, the top edge 108 of the body 102 can be positioned below the top edge 88 of the primary packaging 80, i.e., the body 102 can be positioned such that the top edge 88 of the primary packaging 80 extends beyond the top edge 108 of the body 102. In an embodiment, as shown in FIG. 2C the label system 100 can be provided without one or both of the right handle 130 and the left handle 140 and include one or more of the body 102, the tear line 120, and the tear stop 122.

In an embodiment, a length (L) of the body 102 is equal to or less than a length (L2) of the primary packaging 80. For example, the length (L) of the body 102 can be between 10% and 100% of the length (L2) of the primary packaging 80. However, it will be appreciated that greater or lesser lengths (L) of the body 102 are also contemplated. In an embodiment, a width (W) of the body 102 is equal to or less than a width (W2) of the primary packaging 80. For example, a width (W) of the body 102 can be between 10% and 100% of the width (W2) of the primary packaging 80. However, it will be appreciated that greater or lesser width (W) of the body 102 are also contemplated.

In an exemplary method of manufacture, a primary packaging 80 is provided defining an interior cavity that defines a sterile environment and includes a medical device 50 disposed therein. A label system 100 is coupled to the primary packaging by coupling a surface of the body 102 of the label system 100 with a surface of the primary packaging 80. A top edge 108 of the body is aligned with a top edge 88 of the primary packaging 80.

In an embodiment, a cut 124 can be made through one or both of a portion of the seal 82 of the primary packaging 80 and a portion of the body 102. The cut 124 extends downwards from the top edge 88 of the primary packaging 80, and/or the top edge 108 of the body 102 and is aligned with the tear line 120 and/or disposed between the right handle 130 and the left handle 140. The cut 124 extends to a point that is above the bottom edge of the seal 82. In an embodiment, the cut 124 extends a distance that is less than half the height of the seal 82. As such the cut 124 does not compromise the sterile environment defined by the primary packaging 80 but can facilitate opening the primary packaging as described in more detail herein. In an embodiment, the cut line 124 is disposed 1.5 cm from one of the left edge or the right edge of the body 102 or the primary packaging 80. However, it will be appreciated that greater or lesser distances are also contemplated. In an embodiment, the cut line 124 extends 0.5 cm from a top edge 88. However, it will be appreciated that greater or lesser distances are also contemplated. In an embodiment, the cut 124 defines a straight line cut, or a shaped notch such as a triangular notch or "V"-notch, a square notch, a rectangular notch, a semi-circular notch, or similar suitably shaped notch without limitation.

Figure 2E:
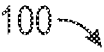
FIG. 2E shows a perspective view of a label system with an offset tear line in an assembled state with a packaging system, in accordance with embodiments disclosed herein.
Figure 2E:
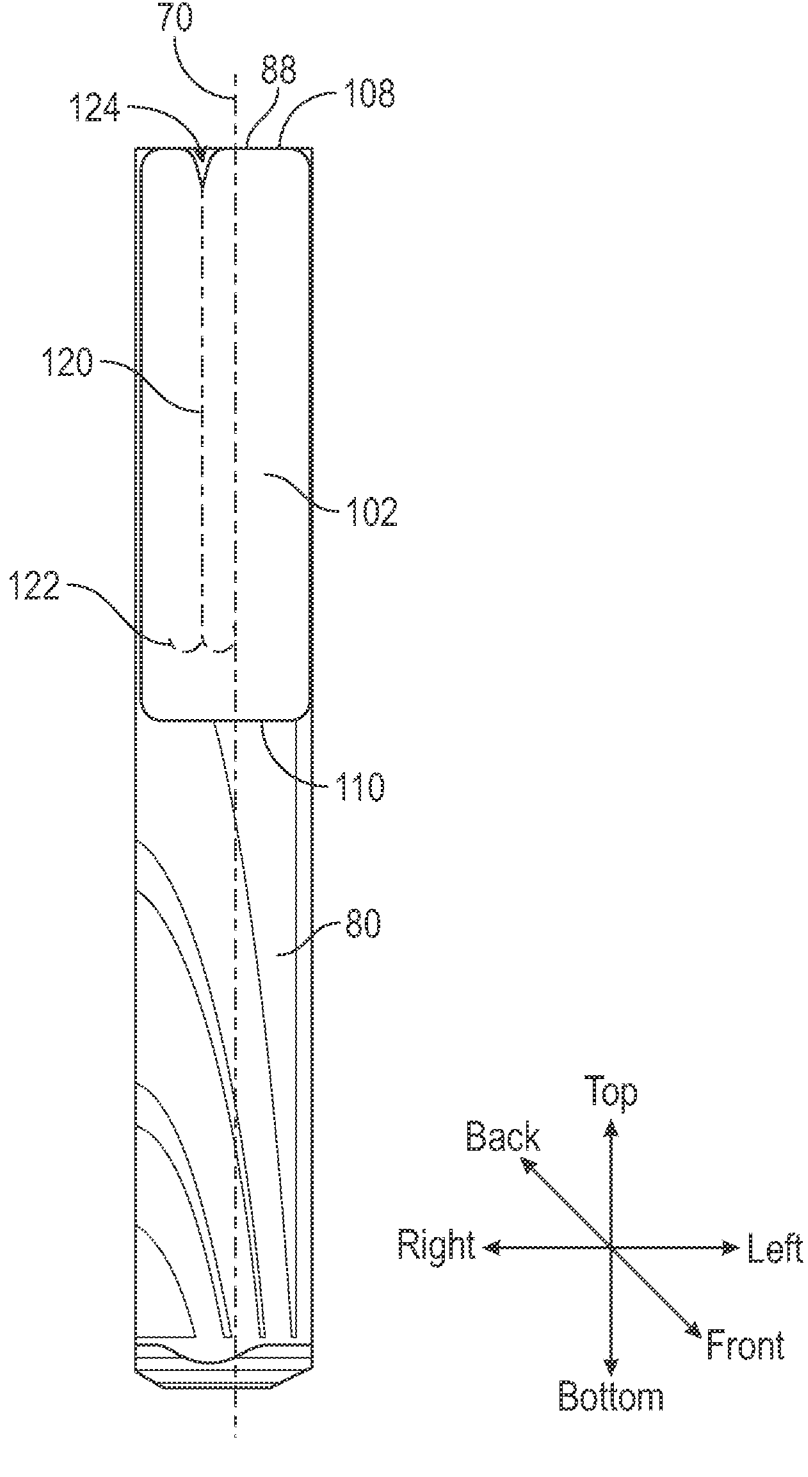

In an embodiment, as shown in FIGS. 1 and 2A, one or both of the tear line 120 and a cut line 124 are disposed centrally on the body 102, equidistant from a right edge and a left edge of the body 102. In an embodiment, one or both of the tear line 120 and the cut line 124 can be disposed to either a left side or a right side of the central position on the body 102, i.e., disposed closer to a left edge or closer to a right edge of the body 102. For example, as shown in FIG. 2E, the tear line 120 and the cut line 124 are disposed to a left side of a central longitudinal axis 70 of the label system 100.

In an exemplary method of use, as shown in FIG. 2A, a label and packaging system 90 is provided including a label system 100 coupled to a primary packaging 80, as described herein. A medical device 50 is contained within the primary packaging 80 in a sterile environment. A user can grasp the label system 100 by grasping the right handle 130 and the left handle 140. For example, a user can place a first digit through the aperture 132 of the right handle 130 and a second digit through the aperture 142 of the left handle 140. The user can then urge the right handle 130 and the left handle 140 in opposite directions, for example in opposite directions along the frontal axis, the sagittal axis, or along an axis extending at an angle thereto. One or both of the cut 124 and the tear line 120 facilitate separation of a right portion of the body 102 and a left portion of the body 102 as the right handle 130 and the left handle 140 are urged in opposite directions. One or both of the cut 124 and the tear line 120 facilitate separation of a right portion of the primary packaging 80 and a left portion of the packaging 80 as the right handle 130 and the left handle 140 are urged in opposite directions.

A user can continue to separate the body 102 and the packaging 80 along the tear line 120 up until the bottom end of the tear line 120 is reached. In an embodiment, the body 102 further includes a tear stop 122 to prevent further separation beyond the bottom end of the tear line 120. Advantageously, the tear line 120 and optionally the tear stop 122 guides the separation of the body 102 and the primary packaging 80 to a predetermined distance, e.g., distance (d). This allows the user to open the primary packaging 80 and access the medical device 50 while still allowing the primary packaging 80 to retain the medical device 50 therein. For example, if the packaging 80 were allowed to separate along a majority or an entire length (L2) of the packaging 80, the medical device 50 would fall out of the packaging 80 and compromise the sterility of the medical device 50, e.g., by falling on the floor or a non-sterile surface. Further, the user would be unable to return the medical device 50 to the primary packaging 80 after use to contain any mess and facilitate disposal. By contrast, the label system 100 restricts separation to a predefined length and/or path, maintaining a portion of the primary packaging 80 intact to define a pocket and to retain the medical device 50 therein.

In an embodiment, the body 102 includes an adhesive disposed on a surface of the body 102, e.g., the front surface 104, and configured to adhere the label system 100 and primary packaging 80 assembly to a surface for ease of use. For example, once the primary packaging 80 has been opened, as described herein, the adhesive front surface 104 allows the label and packaging system 90 to be adhered to a wall at a convenient position to facilitate usage of the medical device 50. In an embodiment, the adhesive front surface 104 facilitates attaching the label and packaging system 90 to a surface to prevent the label system 100 and primary packaging 80 assembly from falling off the surface. In an embodiment, the adhesive surface disposed on the front surface 104 further includes a release layer (not shown) disposed thereon and configured to protect the adhesive surface during transport and storage.

Figure 3C:
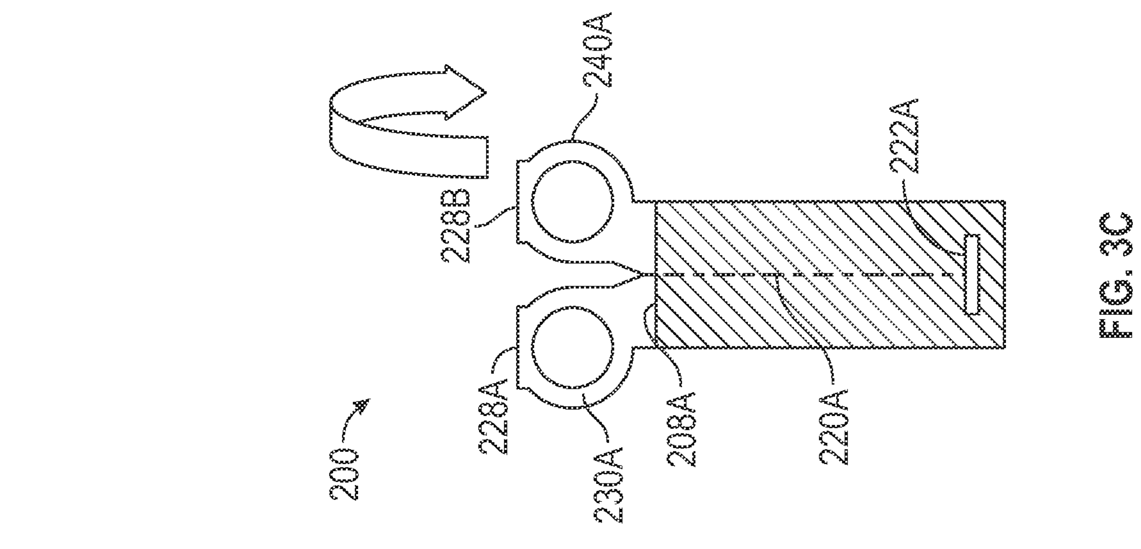
FIG. 3C shows a foldable label system in a folded configuration, in accordance with embodiments disclosed herein.
Figure 3B:
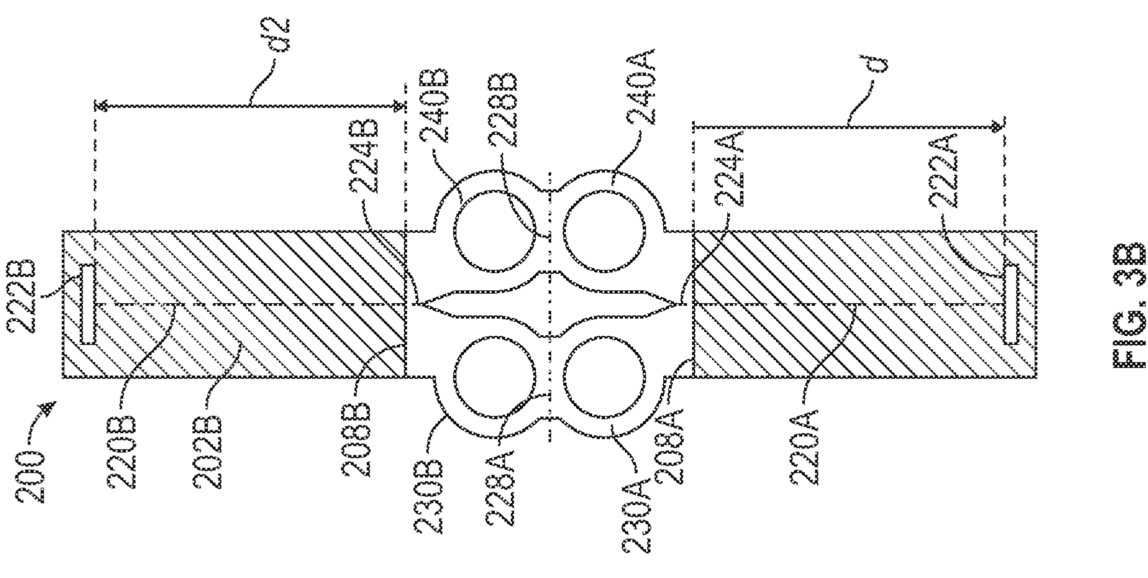
FIGS. 3A-3B show foldable label systems in an unfolded configuration, in accordance with embodiments disclosed herein.
Figure 3A:
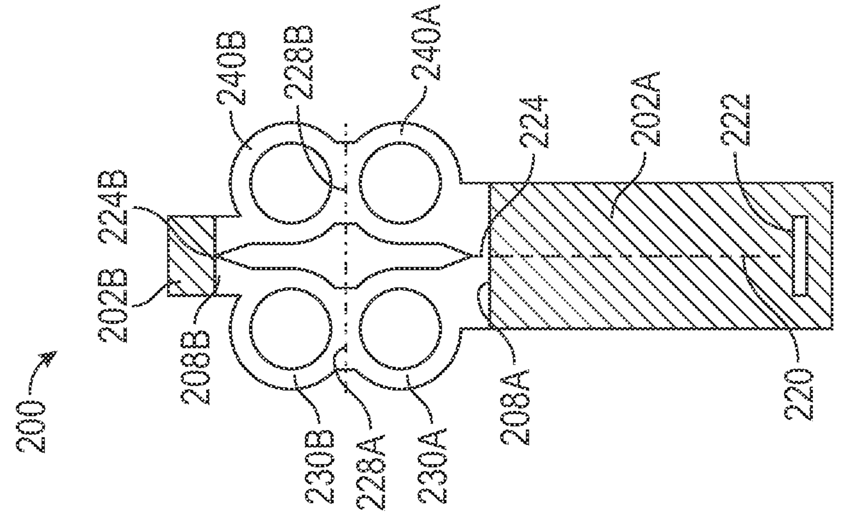

FIGS. 3A-3C show an embodiment of a label system 200 for use with a primary packaging 80 and medical device 50, as described herein. The label system 200 includes a first body 202A, a first right handle 230A, and a first left handle 240A. The first body 202A includes a first tear line 220A extending from a top edge 208A of the first body 202A. The label system 200 further includes a second right handle 230B extending from a top edge of the first right handle 230A and a second left handle 240B extending from a top edge of the first left handle 240A. The label system 200 includes a first fold line 228A extending along a frontal axis and disposed equidistant between the first right handle 230A and the second right handle 230B, and a second fold line 228B disposed equidistant between the first left handle 240A and the second left handle 240B and extending along a frontal axis. The second right handle 230B and the second left handle 240B are coupled to a first edge 208B of the second body 202B.

In an embodiment, the label system 200 can be folded along one or both of the first fold line 228A and the second fold line 228B so that the first right handle 230A aligns with the second right handle 230B, the first left handle 240A aligns with the second left handle 240B and the second body aligns 202B aligns with the first body 202A. For example, one or more of an outer perimeter of the first right handle 230A aligns with the outer perimeter of the second right handle 230B, an outer perimeter of the first left handle 240A aligns with the outer perimeter of the second left handle 240B, an aperture of the first right handle 230A aligns with an aperture of the second right handle 230B, an aperture of the first left handle 240A aligns with the aperture of the second left handle 240B, and the first edge 208B of the second body 202B aligns with the top edge 208A of the first body 202A, or combinations thereof.

In an embodiment, a surface of the first right handle 230A is coupled with a surface of the second right handle 230B, and a surface of the first left handle 240A is coupled with a surface of the second left handle 240B, using adhesive sealing, mechanical sealing, energized sealing such as heat sealing, ultrasonic welding, combinations thereof, or the like. In an embodiment, a surface of the first body 202A is coupled with a front surface of the primary packaging 80 and a surface of the second body 202B is coupled with a rear surface of the primary packaging 80 using adhesive sealing, mechanical sealing, energized sealing such as heat sealing, ultrasonic welding, combinations thereof, or the like. For example, one or both of the first body 202A and the second body 202B includes an adhesive disposed on a surface thereof. As shown in FIG. 3C, as the label system 200 is folded along the first fold line 228A and the second fold line 228B, the first body 202A can be adhered to a front side of the primary packaging 80 and the second body 202B can be adhered to the rear side of the primary packaging 80.

In an embodiment, as shown in FIG. 3A, the first body 202A and the second body 202B can be of different dimensions, i.e., a length and/or width that are different from the length (L) and/or width (W) of the first body 202A. In an embodiment, as shown in FIG. 3B, the first body 202A and the second body 202B can be of the same dimensions, i.e., having a length (L) and/or width (W) that are the same. In an embodiment, as shown in FIG. 3A, the first body 202A can include one or more of a tear line 220, a tear stop 222 and a cut 224.

In an embodiment, as shown in FIG. 3B, the first body 202A includes one or more of a first tear line 220A, a first tear stop 222A, and a first cut 224A and the second body 202B includes one or more of a second tear line 220B, a second tear stop 222B, and a second cut 224B. In an embodiment, the second tear line 220B extends along a second distance (d2). The second distance of the second tear line 220B can be the same or different from the distance (d) of the first tear line 220A.

In an exemplary method of use, as shown in FIG. 3C, the first right handle 230A and the second right handle 230B can be moved in an opposite direction from the first left handle 240A and the second left handle 240B to tear both the first body 202A and the second body 202B along at least the first tear line 220A to separate both the first body 202A and the second body 202B and the primary packaging 80 disposed therebetween.

Advantageously, the label system(s) 100, 200 can be applied to the primary packaging 80 after formation of the primary packaging 80. This allows the labeling system, which facilitates opening of the primary packaging, to be added at a later time, e.g., retrofitted to existing products before sale, or fitted to the packaging by an end user that has reduced dexterity. The label system(s) can be modified to display different information about the primary packaging 80 and/or medical device 50 disposed therein, and fitted to the primary packaging 80 after formation of the primary packaging 80. Exemplary information can include information about the brand, make, model, serial number, batch number of the medical device, instructions for use, instructions on how to open, instructions for disposal, or the like. Advantageously, the label system(s) 100, 200 can include instructions printed thereon to indicate how to use the label system(s) 100, 200 to open the primary packaging 80, e.g. to assist in which end to open the primary packaging 80, where to start the separation along the tear line 120, or at cut line 124, how to hole finger handle 130, 140, etc.

Advantageously, a single type of label system, e.g., one of the label systems 100, 200, can be coupled to various types, sizes, and shapes, of primary packaging 80 simplifying manufacturing and reducing associated costs. Advantageously, the labeling system(s) 100, 200 can indicate to a user which is the correct end to open the primary packaging 80, i.e., to begin opening the primary packaging 80 from a top edge 88, adjacent the non-sterile portion 54 of the medical device 50. This mitigates a user accidentally opening the primary packaging 80 from a different edge that is not adjacent the non-sterile portion 54 and compromising the sterility of the sterile portion 52.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A labeling and packaging system, comprising:
- a primary packaging having a top seam and a bottom seam and defining an interior cavity;
- a medical device disposed within the interior cavity; and
- a label system, comprising:
  - a first body extending over a frontal plane and defining a front surface and a rear surface and having a length (L) and a width (W), the rear surface coupled to a front outer surface of the primary packaging;
  - a first right handle coupled to a right side of a top edge of the first body;
  - a second right handle extending from a top edge of the first right handle and including a first fold line disposed therebetween;
  - a first left handle coupled to a left side of the top edge of the first body;
  - a second left handle extending from a top edge of the first left handle and including a second fold line disposed therebetween;
  - a second body, coupled to both the second right handle and the second left handle along a first edge of the second body;
  - a first tear line extending longitudinally from the top edge of the first body, between the first right handle and the first left handle, the first tear line having a distance (d) that is less than the length (L) of the first body, the first tear line configured to facilitate separation there along when the first right handle is urged in an opposite direction from the first left handle; and
  - a second tear line extending from the first edge of the second body along a second distance (d2).

2. The system according to claim 1, wherein the distance (d) is between 20% and 80% of the length (L) of the first body.

3. The system according to claim 2, wherein the length (L) of the first body is equal to or less than a second length (L2) of the primary packaging.

4. The system according to claim 1, further including a tear stop disposed at a bottom end of the first tear line.

5. The system according to claim 4, wherein the tear stop includes a reinforcement displaying an increased tensile strength to prevent further separation of the first body.

6. The system according to claim 4, wherein the tear stop includes a frangible line angled relative to the first tear line and configured to mitigate further separation along the first tear line at a predetermined position on the primary packaging.

7. The system according to claim 1, further including a cut extending from the top edge of the first body and disposed between the first right handle and the first left handle, the cut extending through one or both of a portion of the first body and a portion of the top seam of the primary packaging.

8. The system according to claim 1, wherein the rear surface is coupled to the front outer surface of the primary packaging by one or more of adhesive sealing, mechanical sealing, energized sealing, heat sealing, and ultrasonic welding.

9. The system according to claim 1, wherein an outer perimeter of the second right handle aligns with an outer perimeter of the first right handle when folded along the first fold line, and an outer perimeter of the second left handle aligns with an outer perimeter of the first left handle when folded along the second fold line, and a surface of the second body is configured to couple with a rear side of the primary packaging.

10. A method of opening a packaging and label system, comprising:
- providing a primary packaging having a top seam and a bottom seam and defining an interior cavity, a medical device disposed within the interior cavity, and a label system having a first body, a rear surface of the first body coupled with a front outer surface of the primary packaging;
- grasping a first right handle, a second right handle, a first left handle and a second left handle of the label system, wherein;
  - the first right handle is coupled to a right side of a top edge of the first body;
  - the second right handle extends from a top edge of the first right handle and includes a first fold line disposed therebetween;
  - the first left handle is coupled to a left side of the top edge of the first body;
  - the second left handle extends from a top edge of the first left handle and includes a second fold line disposed therebetween; and
  - a second body is coupled to both the second right handle and the second left handle along a first edge of the second body;
- urging the first right handle and the second right handle in an opposite direction from the first left handle and the second left handle along an axis extending at an angle relative to a longitudinal axis of the primary packaging;
- separating the first body along a first tear line and separating the second body along a second tear line, each tear line extending longitudinally; and
- tearing a portion of the primary packaging to access the medical device.

11. The method according to claim 10, wherein in the first tear line is a line of weakness extending along the first body by a distance (d) to facilitate separation therealong, the distance (d) being less than a longitudinal length (L) of the first body.

12. The method according to claim 11, wherein the distance (d) of the first tear line is less than a second longitudinal length (L2) of the primary packaging.

13. The method according to claim 11, further including a tear stop disposed at a bottom end of the first tear line and configured to prevent further separation of the first body beyond the distance (d).

14. The method according to claim 13, wherein the tear stop includes one of a reinforcement or a frangible line angled relative to the first tear line and configured to mitigate further separation along the first tear line at a predetermined position on the primary packaging.

15. The method according to claim 10, wherein coupling the rear surface of the first body to the front outer surface of the primary packaging includes one or more of adhesive sealing, mechanical sealing, energized sealing, heat sealing, and ultrasonic welding.

16. A method of manufacturing a label and packaging system, comprising:

forming a primary packaging having a top seam and a bottom seam, a front outer surface and a rear outer surface, the primary packaging defining an interior cavity containing a medical device; and coupling a rear surface of a first body of a labeling system to the front outer surface of the primary packaging, the labeling system comprising:

a first right handle extending from a right side of a top edge of the first body, a second right handle extending from a top edge of the first right handle and including a first fold line disposed therebetween;

a first left handle extending from a left side of the top edge of the first body;

a second left handle extending from a top edge of the first left handle and including a second fold line disposed therebetween;

a second body, coupled to both the second right handle and the second left handle along a first edge of the second body;

a first tear line extending longitudinally from the top edge of the first body, between the first right handle and the first left handle; and a second tear line extending from the first edge of the second body along a second distance.

17. The method according to claim 16, further including folding the second right handle relative to the first right handle along the first fold line such that an outer perimeter of the second right handle aligns with the outer perimeter of the first right handle, and folding the second left handle relative to the first left handle along the second fold line such that an outer perimeter of the second left handle aligns with the outer perimeter of the first left handle.

18. The method according to claim 17, further including coupling a surface of the second body to the rear outer surface of the primary packaging.

19. The method according to claim 17, wherein coupling the rear surface of the first body to the front outer surface of the primary packaging includes one or more of adhesive sealing, mechanical sealing, energized sealing, heat sealing, and ultrasonic welding.

20. The method according to claim 16, further including forming a cut disposed between the first right handle and the first left handle and extending from the top edge of the first body, the cut extending through one or both of the first body and a portion of the top seam.

* * * * *